US012115024B2

(12) United States Patent
Di Ianni et al.

(10) Patent No.: US 12,115,024 B2
(45) Date of Patent: Oct. 15, 2024

(54) FUNCTIONAL ULTRASOUND IMAGING OF THE BRAIN USING DEEP LEARNING AND SPARSE DATA

(71) Applicant: The Board of Trustees of the Leland Stanford Junior University, Stanford, CA (US)

(72) Inventors: Tommaso Di Ianni, San Francisco, CA (US); Raag D. Airan, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 154 days.

(21) Appl. No.: 17/488,722

(22) Filed: Sep. 29, 2021

(65) Prior Publication Data
US 2022/0096055 A1 Mar. 31, 2022

Related U.S. Application Data

(60) Provisional application No. 63/084,816, filed on Sep. 29, 2020.

(51) Int. Cl.
*A61B 8/00* (2006.01)
*A61B 8/06* (2006.01)
*A61B 8/08* (2006.01)

(52) U.S. Cl.
CPC .............. *A61B 8/5207* (2013.01); *A61B 8/06* (2013.01); *A61B 8/488* (2013.01); *A61B 8/5276* (2013.01)

(58) Field of Classification Search
CPC ......... A61B 8/5207; A61B 8/06; A61B 8/488; A61B 8/5276; A61B 8/0808; A61B 8/5223
See application file for complete search history.

(56) References Cited

U.S. PATENT DOCUMENTS

| 10,242,443 B2 | 3/2019 | Hsieh |
| 2018/0284250 A1* | 10/2018 | Bjaerum ............. G01S 7/52085 |

(Continued)

FOREIGN PATENT DOCUMENTS

| WO | WO2012131418 A1 | 10/2012 | |
| WO | WO-2020002620 A1 * | 1/2020 | ............... A61B 8/08 |

OTHER PUBLICATIONS

Z. Zhou, Y. Wang, Y. Guo, X. Jiang and Y. Qi, "Ultrafast Plane Wave Imaging With Line-Scan-Quality Using an Ultrasound-Transfer Generative Adversarial Network," in IEEE Journal of Biomedical and Health Informatics, vol. 24, No. 4, pp. 943-956, Apr. 2020, doi: 10.1109/JBHI.2019.2950334. (Year: 2020).*

(Continued)

*Primary Examiner* — Joel Lamprecht
*Assistant Examiner* — James F McDonald, III
(74) *Attorney, Agent, or Firm* — LUMEN PATENT FIRM

(57) ABSTRACT

A method for ultrasound power Doppler image reconstruction includes obtaining sparse sequences of compound frames of ultrasound data; inputting the sparse sequences into a convolutional neural network; and generating as output from the convolutional neural network a reconstructed time series of power Doppler images corresponding to the sparse sequences. The convolutional neural network is trained using a custom loss function to learn a reconstruction function using ground truth images from high-quality in vivo images.

6 Claims, 14 Drawing Sheets

(56) References Cited

U.S. PATENT DOCUMENTS

| | | | | |
|---|---|---|---|---|
| 2019/0122073 A1* | 4/2019 | Ozdemir | ................ | G06V 20/56 |
| 2019/0175138 A1* | 6/2019 | Torp | .................... | A61B 8/4236 |
| 2019/0336033 A1* | 11/2019 | Takeshima | ......... | G01R 33/5608 |
| 2020/0151513 A1* | 5/2020 | Lee | ...................... | G06V 10/764 |
| 2020/0234461 A1* | 7/2020 | Osumi | ................... | G06T 7/136 |

OTHER PUBLICATIONS

Y. H. Yoon, S. Khan, J. Huh and J. C. Ye, "Efficient B-Mode Ultrasound Image Reconstruction From Sub-Sampled RF Data Using Deep Learning," in IEEE Transactions on Medical Imaging, vol. 38, No. 2, pp. 325-336, Feb. 2019, doi: 10.1109/TMI.2018. 2864821. (Year: 2019).*

Ravishankar et al., Image Reconstruction: From Sparsity to Data-adaptive Methods and Machine Learning, arXiv:1904.02816v3, Aug. 16, 2019.

Perdios et al., CNN-Based Image Reconstruction Method for Ultra-fast Ultrasound Imaging, arXiv:2008.12750v1, Aug. 28, 2020.

AMCervUS—Machine learning for ultrafast vascular and functional ultrasound imaging of the brain. Accessed Sep. 29, 2021 at https://dim-elicit.fr/en/project/amcervus/.

Yoon et al., Efficient B-mode Ultrasound Image Reconstruction from Sub-sampled RF Data using Deep Learning, arXiv:1712. 06096v3, Aug. 7, 2018.

* cited by examiner

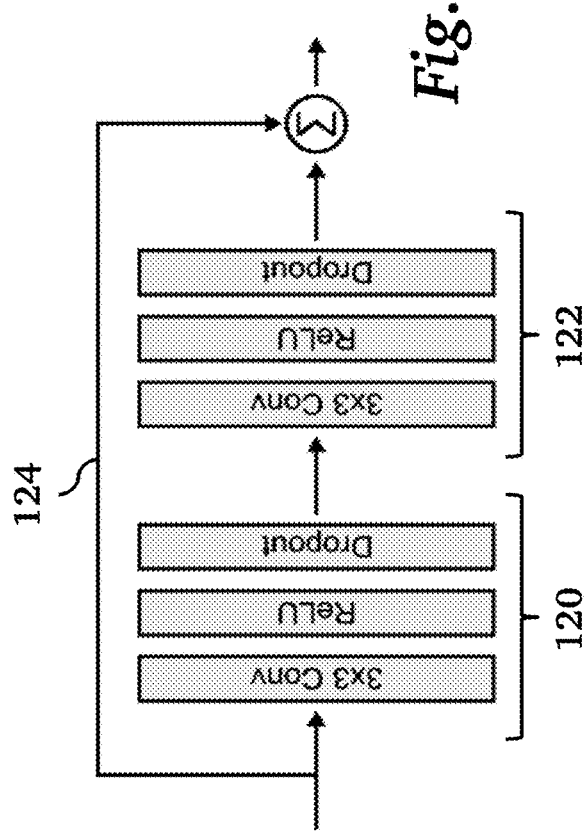
*Fig. 1C*
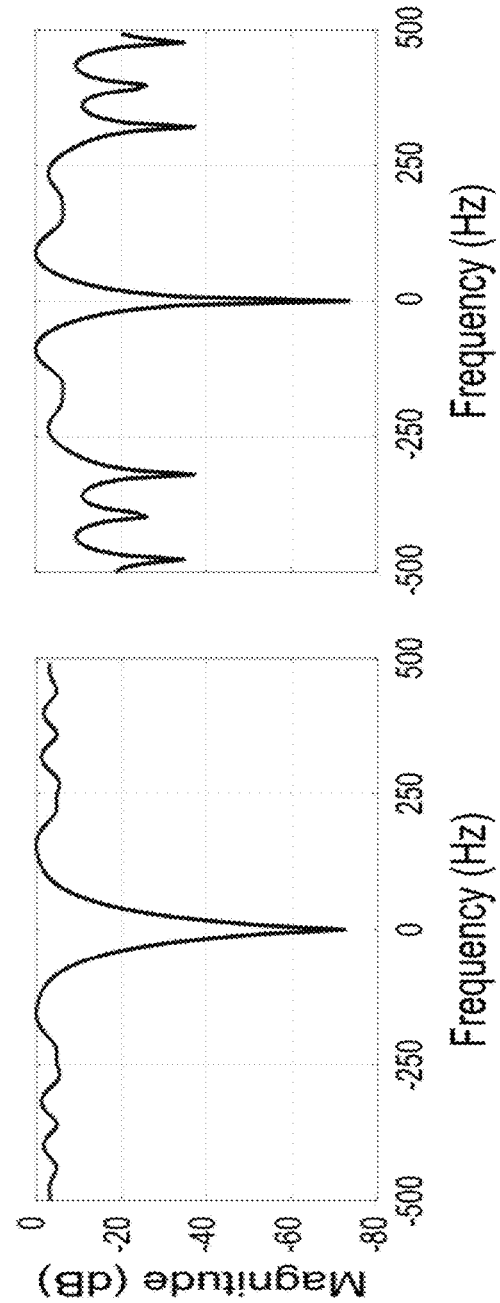
*Fig. 1D*
*Fig. 1E*

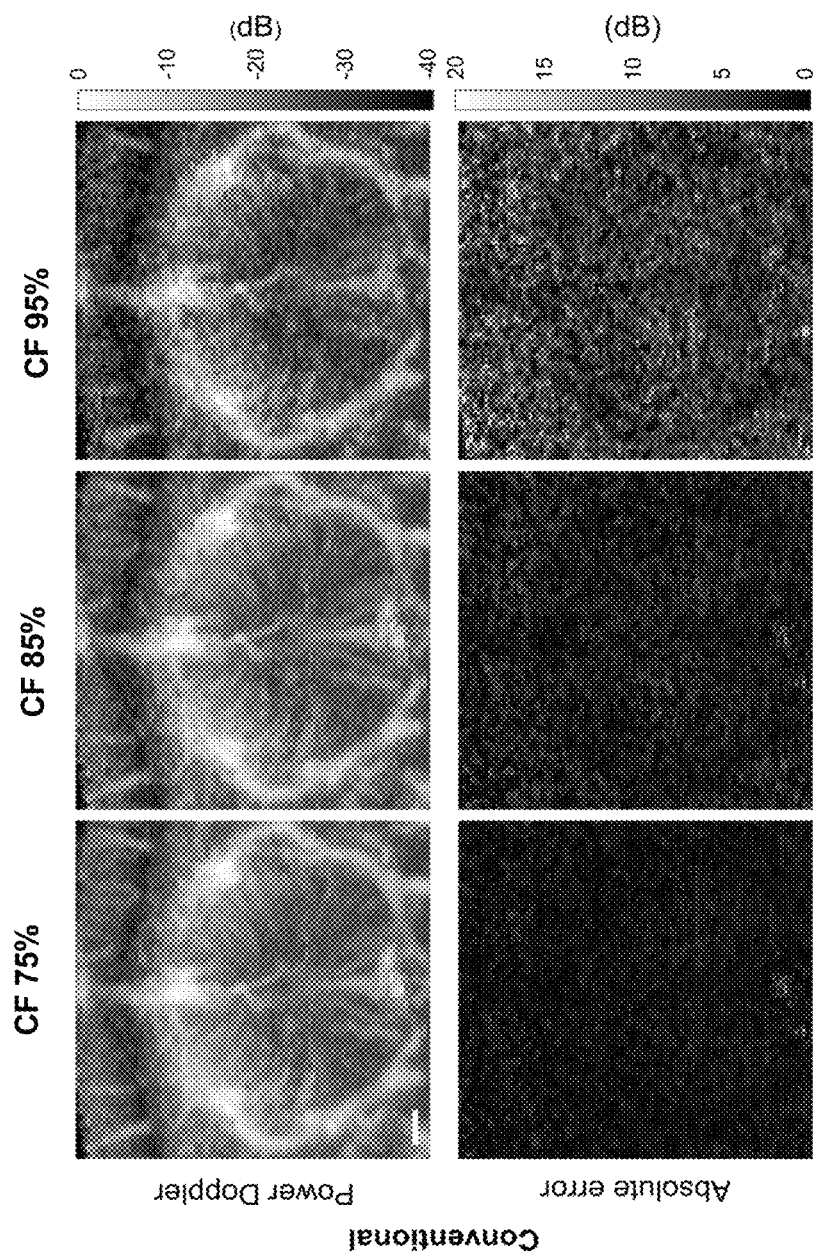

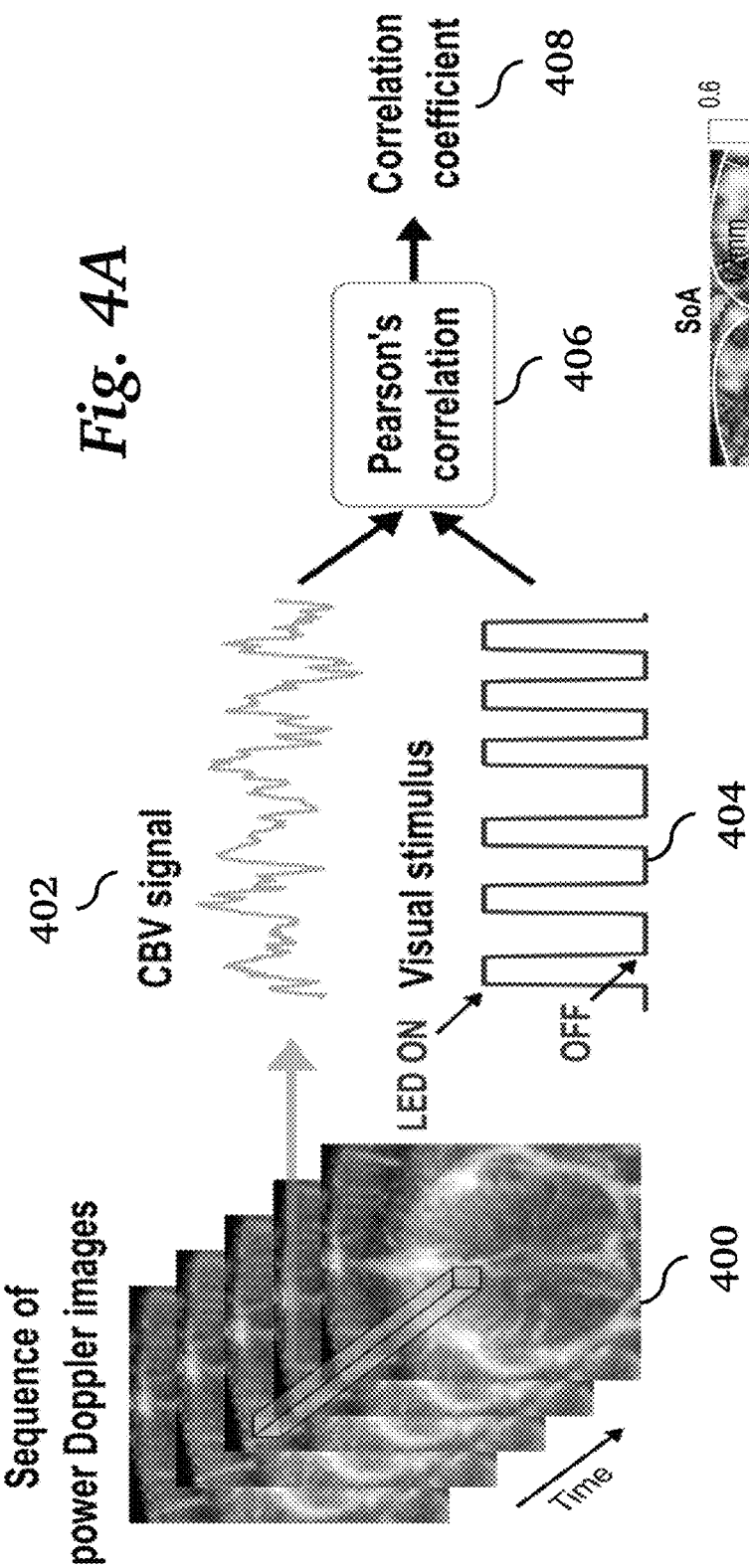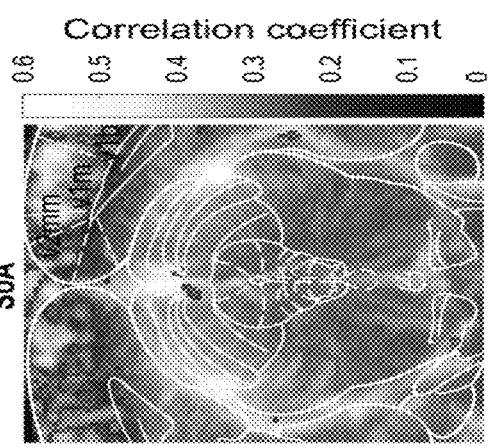
Fig. 4A
Fig. 4B

*Fig. 5A*  *Fig. 5B*
CF 95%; m = 1/2; k = 50    CF 95%; m = 1/4; k = 100
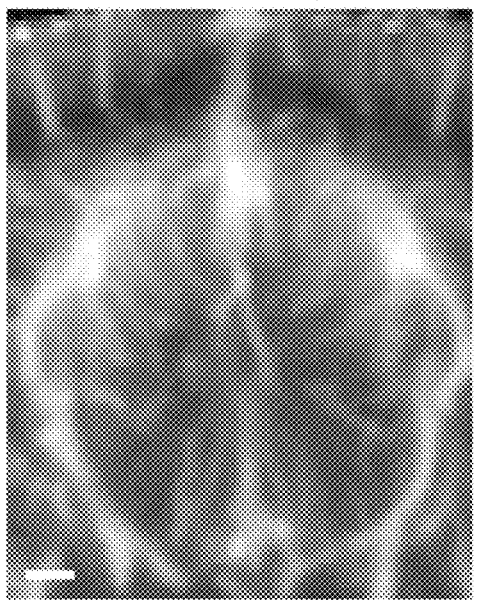 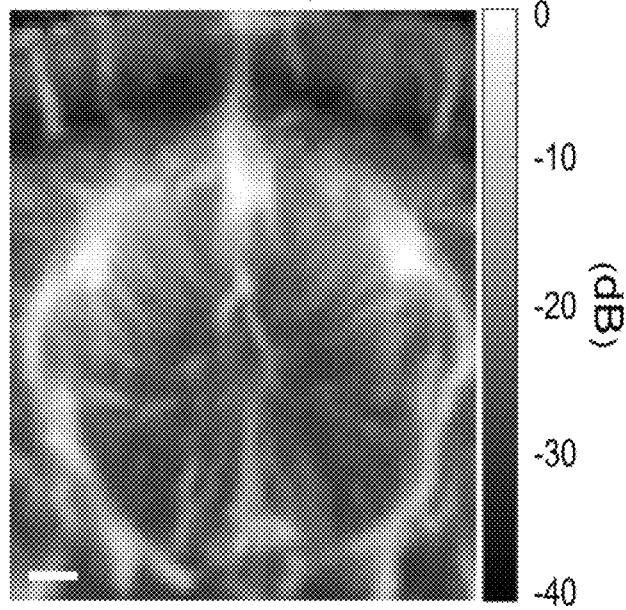
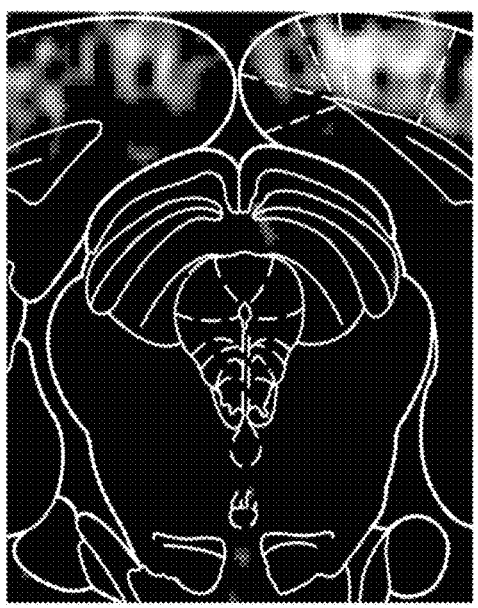 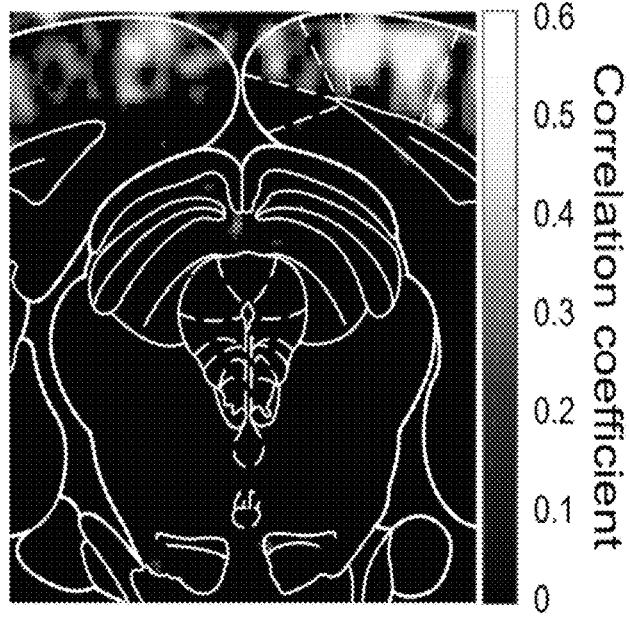

FUNCTIONAL ULTRASOUND IMAGING OF THE BRAIN USING DEEP LEARNING AND SPARSE DATA

CROSS-REFERENCE TO RELATED APPLICATIONS

This application claims priority from U.S. Provisional Patent Application 63/084,816 filed Sep. 29, 2020, which is incorporated herein by reference.

STATEMENT OF FEDERALLY SPONSORED RESEARCH

None.

FIELD OF THE INVENTION

The present invention relates generally to ultrasound imaging. More specifically, it relates to image reconstruction techniques in functional ultrasound.

BACKGROUND OF THE INVENTION

Functional ultrasound (fUS) imaging is rapidly establishing itself as a state-of-the-art neuroimaging modality owing to its ability to image neural activation in awake and mobile rodents, its relatively low cost, and its unequaled portability. To achieve sufficient blood flow sensitivity in the brain microvasculature, functional ultrasound relies on long sequences of ultrasound data acquisitions at high frame rates, which poses high demands on the sampling and processing hardware, effectively limiting the usability and clinical translation of this imaging modality.

SUMMARY OF THE INVENTION

In one aspect, the present invention provides an image reconstruction approach based on deep learning that significantly reduces the amount of ultrasound data necessary while retaining the imaging performance.

A convolutional neural network is trained to learn the power Doppler reconstruction function from sparse sequences of compound ultrasound data with a compression factor up to 95%. The training is performed using ground truth images from high-quality in vivo acquisitions, and with a custom loss function.

The trained network produces highly accurate images and restores the sensitivity in the smaller blood vessels even when using heavily undersampled data. Time series of power Doppler images can be reconstructed with sufficient accuracy to detect the small changes in cerebral blood volume (~10%) characteristic of task-evoked cortical activation, even though the network was not formally trained to reconstruct such image series.

The platform may facilitate the development of this neuroimaging modality in any setting where dedicated hardware is not available or in clinical scanners. The network performance was tested in a task-evoked functional neuroimaging application, demonstrating that time series of power Doppler images can be reconstructed with adequate accuracy to compute functional activity maps. Notably, the network reduces the occurrence of motion artefacts in awake functional ultrasound imaging experiments.

The main advantage of using sparse sequences is the net reduction in processing time and computational capacity demands. The approach can facilitate the development of functional ultrasound neuroimaging in any setting where dedicated hardware is not available or even on clinical scanners, making this technology more affordable and opening the way to new potential applications based on this imaging modality. Additionally, sparse sequences can prove beneficial in experimental situations where functional ultrasound emissions need to be interleaved with therapeutic ultrasound pulses, such as in the monitoring of focused ultrasound neurointerventions.

The technique can be readily adapted to other high-framerate Doppler ultrasound imaging modalities, including color and vector Doppler flow imaging, to expedite their deployment in ultrasound systems.

The technique can be applied to using power Doppler images for intrasurgical guidance and monitoring. Using conventional techniques for reconstructing the power Doppler images is limited to only a few image acquisitions during the entire surgery, and the images need to be processed offline due to the high amount of data and computational power required. Using the present techniques, in contrast, the image acquisition and reconstruction is much more efficient, and potentially the imaging can be performed in real-time.

In one aspect, the invention provides a method for ultrasound power Doppler image reconstruction comprising: obtaining sparse sequences of compound frames of ultrasound data; inputting the sparse sequences into a convolutional neural network; generating as output from the convolutional neural network a reconstructed time series of power Doppler images corresponding to the sparse sequences; wherein the convolutional neural network is trained using a custom loss function to learn a reconstruction function using ground truth images from high-quality in vivo images.

Preferably, the convolutional neural network is a U-Net with drop-out layers. More preferably, the convolutional neural network is a U-Net with an input layer of 3D is convolutional filters that extract spatiotemporal features from the sparse sequences. The custom loss function is preferably defined as the weighted sum of 1) the mean absolute error between the predicted Deep-fUS image and the respective ground truth (LMAE) and 2) a structural dissimilarity index metric loss (LSSIM).

In some applications, the ultrasound power Doppler image reconstruction is performed intrasurgically for guidance and monitoring. In some applications, the ultrasound power Doppler image reconstruction is performed in procedures in newborn through the fontanel window by substantially reducing data acquisition, storage, and processing resources, and by reducing sensitivity to motion artifacts.

BRIEF DESCRIPTION OF THE DRAWINGS

FIG. 1C illustrates the structure of residual blocks in the architecture shown in FIG. 1B.

FIG. 1D and FIG. 1E are graphs of magnitude vs frequency showing representative transfer functions of input 3-D convolutional filters learned by the network according to an embodiment of the present invention.

FIG. 2C is a collection of images showing Power Doppler images reconstructed with the conventional processing using under-sampled compound data (top row) and respective absolute error images (bottom row) with compression factor (CF) 75%, 85%, and 95%.

FIG. 4A is a processing pipeline illustrating how time series sequence of power Doppler images producing cerebral blood volume (CBV) signals are correlated with a stimulus pattern to produce a correlation coefficient.

FIG. 4B is a State-of-the-art (SoA) activation map computed using power Doppler images reconstructed by the conventional approach using 250 complex compound frames.

FIG. 5A-B show representative power Doppler test images and activation maps computed with spatially under-sampled sequences with spatial sampling ratio m=½ (FIG. 5A) and m=¼ (FIG. 5B).

DETAILED DESCRIPTION OF THE INVENTION

Introduction

Functional ultrasound (fUS) is an innovative imaging modality that creates brain-wide neural activity maps at micrometer and millisecond-scale resolution by tracking temporal cerebral blood volume (CBV) changes in the brain microvasculature [1]. Similar to blood oxygen level dependent functional magnetic resonance imaging (BOLD fMRI), the detected CBV signals provide an indirect measurement of local spiking activity via neurovascular coupling [2]. However, fUS has higher spatiotemporal resolution than fMRI and uses more affordable and portable equipment, opening the possibility for functional neuroimaging performed directly at the bedside [3]-[6]. Preclinically, fUS enables imaging of neural activity in awake and freely behaving rodents and reduces the confounding factors introduced by anesthesia/sedation or physical restraint [7], [8]. Furthermore, fUS has proven useful for imaging resting state and task-evoked functional connectivity in the rat and mouse brain [2], [9], [10] and for mapping neural activation in primates during cognition tasks and visual stimulation [11]-[13]. In humans, fUS has been used intraoperatively for image-monitored brain tumor removal surgeries [4], [5], and in neonates to visualize epileptic activity and measure functional connectivity through the anterior fontanel window [3], [6].

Figure 1A:
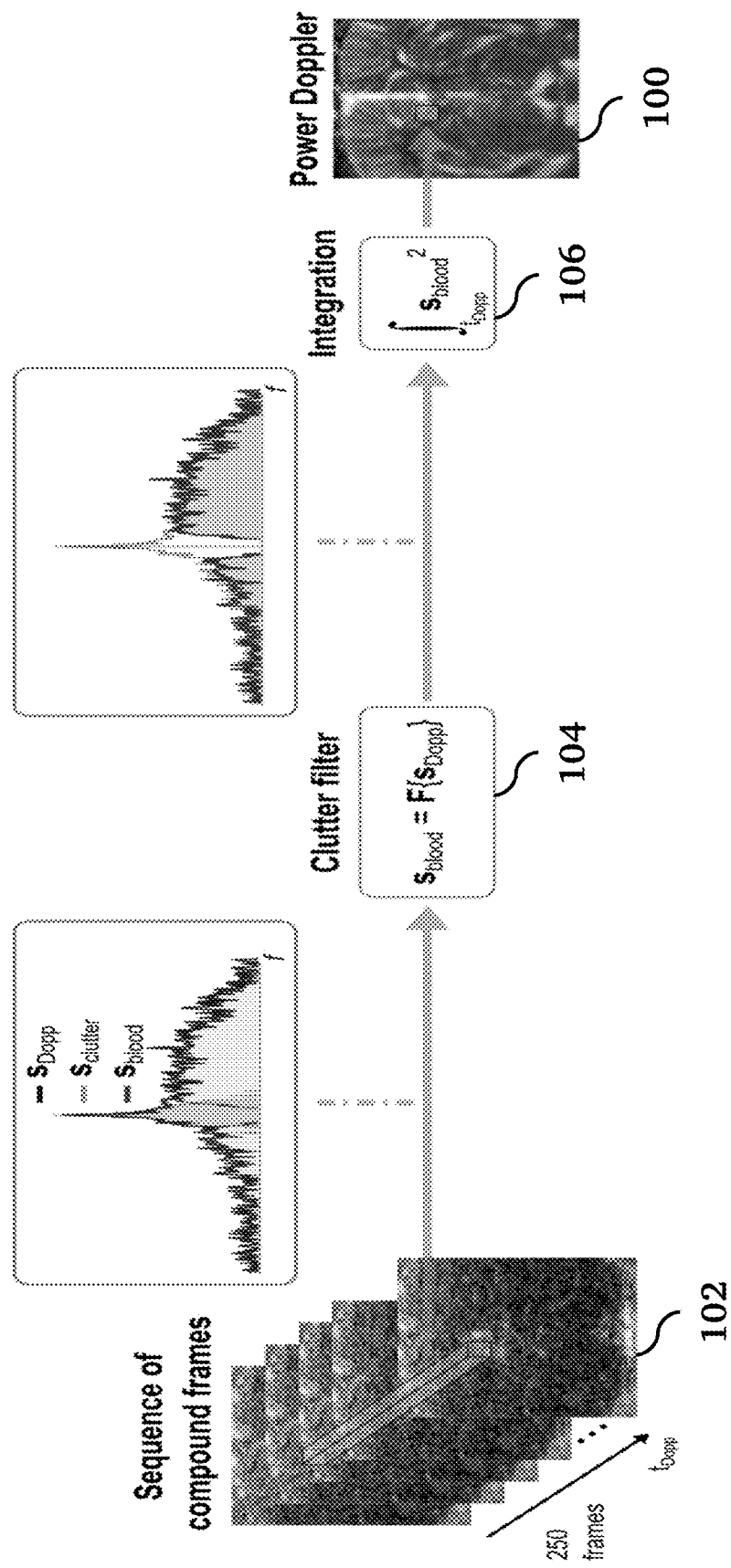
FIG. 1A illustrates a processing pipeline for generating a power Doppler image from a sequence of compound ultrasound frames.

To detect hemodynamic changes in the brain microvascular network, fUS relies on highly sensitive power Doppler sequences based on the use of plane wave emissions. Unfocused ultrasound waves insonify the entire field of view, and the received radiofrequency (RF) data from tilted plane wave emissions are re-focused (or beamformed) and coherently compounded to increase resolution and depth of penetration. This strategy makes it possible to continuously acquire long sequences of ultrasound data at high frame rates. The obtained compound Doppler signals are then processed to filter out the strong, undesired clutter originating from the tissue, and are squared and time-integrated to create power Doppler images with pixel amplitude proportional to the CBV. FIG. 1A illustrates this state-of-the-art processing, where a power Doppler image 100 is created from a sequence of 250 compound ultrasound frames 102. In each pixel, the temporal signal $s_{Dopp}$ sampled in the Doppler time $t_{Dopp}$, is passed through a bank of filters F 104 to remove the tissue clutter component $s_{clutter}$. The retained blood signal $s_{blood}$ is squared and time-integrated 106 to compute the power Doppler pixel value proportional to the cerebral blood volume.

The length of the acquisition sequence is critical to effectively discriminate the weak signals scattered by red blood cells circulating in the blood stream from the strong clutter originating in the surrounding tissue. When long observation windows are used, efficient clutter filtration can be achieved in both large and small vessels by using temporal and singular-value decomposition (SVD) filters [8], [14], [15]. Conversely, this filtration becomes challenging with shorter acquisitions, in particular in the smaller vessels where the blood-signal-to-clutter ratio is reduced and the low-frequency Doppler spectral components overlap with the tissue spectrum. As a result, conventional fUS imaging implementations use hundreds of compound frames (typically 200 to 400) to create a single power Doppler image.

The need to acquire and process large ultrasound datasets poses high demands on the hardware platform in terms of storage capacity and computational power, with data throughputs on the order of 240 MSa/image. These requirements make real-time fUS imaging challenging even in graphics processing unit (GPU) implementations, and these considerations are yet more relevant for volumetric fUS sequences [16], [17]. Importantly, long ultrasound exposure times raise concerns about potential adverse bioeffects, even at diagnostic intensity levels [3], [18]. It is highly desirable to achieve state-of-the-art (SoA) fUS imaging performance with shorter ultrasound acquisitions, as this may effectively improve access to this imaging modality and expedite its clinical translation.

Figure 1B:
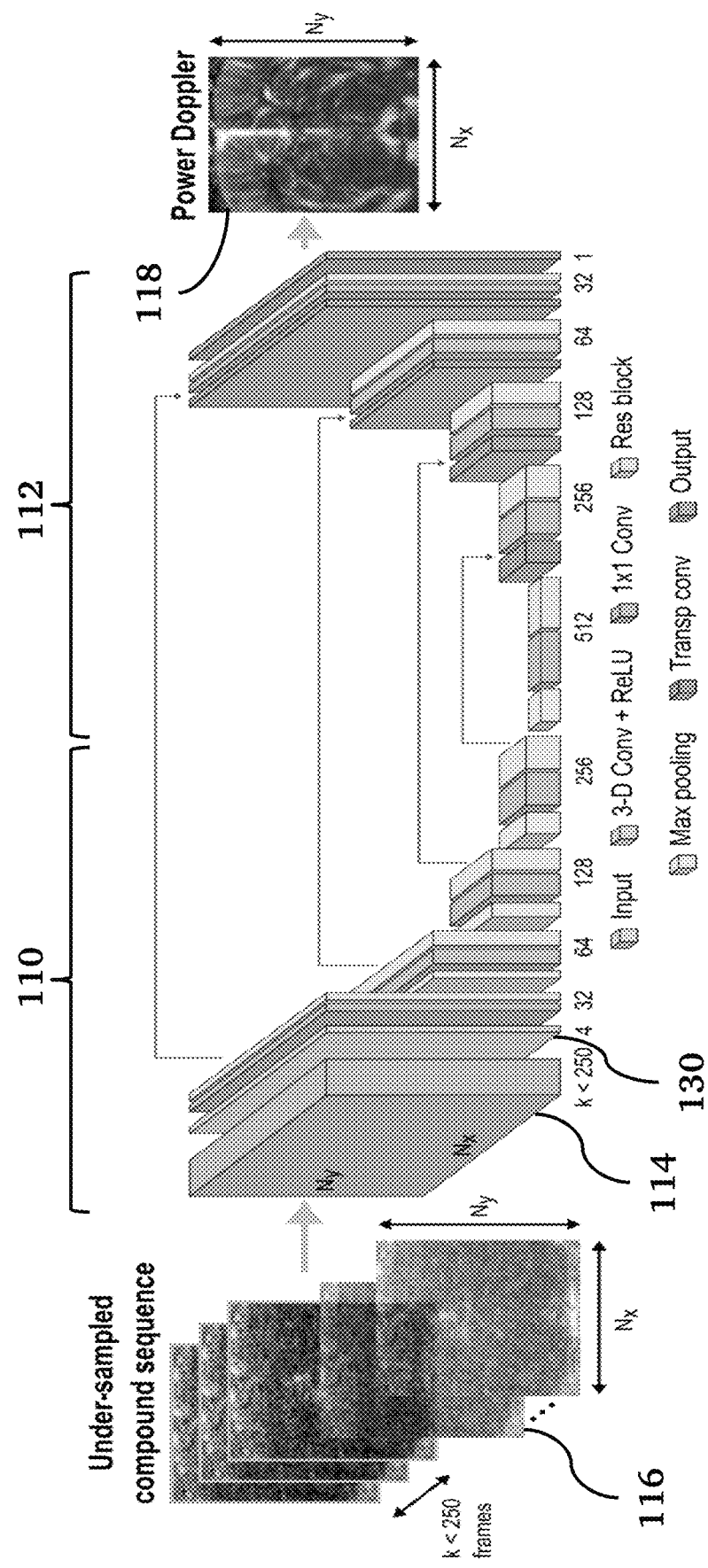
FIG. 1B is an illustration of a deep learning convolutional neural network architecture according to an embodiment of the present invention.

To address these challenges, the inventors have developed a deep learning technique to reconstruct power Doppler images from sparse compound datasets. This technique implements a convolutional neural network (CNN) based on an encoder-decoder architecture (U-Net) with residual connections [19]. Deep learning techniques have been used for biomedical image reconstruction in applications spanning compressed sensing MRI [20], sparse-projection photoacoustic imaging [21], and sparse X-ray computed tomography [22]. Prior CNN applications in medical ultrasound imaging include contrast improvement [23] and image despeckling [24], ultrasound contrast agent localization and tracking [25], [26], and under-sampled and adaptive beamforming [27]-[30]. In the present technique, the network learns a reconstruction mapping between the sparse sequence of compound ultrasound data and the power Doppler output image, without requiring any prior model-based knowledge. The network is trained on high-quality power Doppler images from in vivo acquisitions in rats and using a custom loss function. FIG. 1B illustrates a Deep-fUS architecture used in one embodiment of the invention. It uses a modified U-Net network having residual blocks arranged in a 5-layer encoder 110 followed by a decoder 112. An input 3-D convolutional layer 114 extracts spatiotemporal features from the 3-D input structure. The input data 116 is an under-sampled compound sequence created by selecting the first k frames of $N_x \times N_y$ pixels. The network outputs $N_x \times N_y$ power Doppler images 118. FIG. 1C illustrates the structure of the residual blocks composed of two cascaded Conv/ReLU/Dropout layers 120, 122 implemented with a shortcut connection 124 between the input and output.

Methods

Deep-fUS Network

Our modified U-Net is trained to perform the power Doppler reconstruction task. This fully convolutional neural network is based on an encoder/decoder architecture. The encoder 110 progressively down-samples the input data and learns high-level features that are propagated to the following stages. The decoder 112 uses up-sampling operators to increase the resolution of the encoder features and to consecutively restore the input resolution at the output stage. Skip connections between the encoding and decoding paths allow for retaining context information, which is propagated to the symmetric up-sampling layers.

The modified U-Net is created by adding an input layer 130 composed of four 3-D convolutional filters followed by rectified linear unit (ReLU) activations. This input layer extracts spatiotemporal features from the 3-D input structure, and the transfer functions of the learned filters present a strong rejection of the 0-Hz component, resembling the temporal filters used in the conventional processing approach. FIG. 1D and FIG. 1E show representative transfer functions of the input 3-D convolutional filters learned by the network. These were computed by performing a fast Fourier transform of the filter kernels averaged in the 3×3 spatial domain. The cutoff frequencies (−3 dB) for the two filters are 95 Hz (left) and 58 Hz (right).

In addition, we replaced convolutional layers in the conventional U-net with residual blocks, each having the structure shown in FIG. 1C. As shown in FIG. 1B, residual blocks were arranged in a 5-layer encoder 110 followed by a 4-layer decoder 112 path and implement 3×3 convolutions followed by ReLU activations and a dropout layer to improve regularization. The modified U-net uses 1×1 convolutions at the input of each layer to equalize the number of input and output features of each residual block. In the encoder path, down-sampling is performed by a 2×2 max pooling operator that halves the resolution in both the image dimensions. In the decoder, 2×2 transposed convolutions with ReLU activations are used as up-sampling operators. The number of channels is progressively increased in the encoder (32, 64, 128, 256, and 512 filters) and decreased in the decoder (256, 128, 64, and 32 filters). The output layer is a single-channel 1×1 convolution block. The stride is equal to 1 in all the convolutional layers and 2 in the max pooling and transposed convolution blocks. This network has a total of 9,788,421 trainable parameters (Table 2). The size of the filter kernels in the input stage and the dropout rate were considered as a hyperparameters and were optimized via Bayesian optimization.

All the convolutional kernels were initialized using the He initialization [31].

3D-U-Net, U-Net, and PP-U-Net Networks

In addition to the Deep-fUS network, we trained and optimized three networks. The 3D-U-Net is analogous to Deep-fUS but uses simple convolutional blocks in place of residual blocks. Specifically, each layer is composed of 2 consecutive 3×3 convolution blocks, each followed by ReLU activations and dropout for network regularization. The output layer is a single-channel 1×1 convolution block. The stride is equal to 1 in all the convolutional layers and 2 in the max pooling and transposed convolution blocks. The size of the filter kernels in the first layer and the dropout rate were considered as hyperparameters and were optimized using Bayesian optimization.

The U-Net is analogous to the 3D-U-Net except for the absence of the 3-D convolutional filters at the input. These two networks were independently trained and optimized to separately analyze the effect on the reconstruction performance of the input 3-D convolutional filters and of the residual shortcut connections. In addition, we trained and optimized a network with the same characteristics as the above U-Net to perform the post-processing of power Doppler images that were generated by conventional processing of sparse compound sequences. We refer to this network as PP-U-Net.

All the convolutional kernels were initialized using the He initialization [32].

Datasets

We trained the networks to learn a function y=f(x) that maps the input sequence x of compound frames 116 of $N_x \times N_y$ pixels to the output power Doppler image y 118 of dimensions $N_x \times N_y$. In all our experiments, we used images of 96×96 pixels, and we normalized the input compound datasets. We chose to base the processing on beamformed data instead of sensor RF data to minimize data throughput and storage. SoA images were obtained from in vivo acquisitions of coronal slices of the rat brain reconstructed by state-of-the-art power Doppler processing using 250 complex compound frames. To improve the network regularization, we performed random cropping when more than 96 pixels were available in any image dimension, and a random horizontal flipping was applied with a probability of 50%. In total, we used 740 pairs of compound data and power Doppler images for training, 40 pairs for validation, and 40 pairs for testing the reconstruction performance.

We performed under-sampling of the compound sequences in the temporal domain by selecting the first k frames in each sequence. We retained only the real part of the beamformed data. For the experiments described below in relation to FIG. 5A-B, we also under-sampled the compound frames in the image domain by selecting sub-samples of pixels with a ratio $m = N_{Ret}/N_{Tot}$, with $N_{Ret}$ the number of retained pixels and $N_{Tot} = 96^2$ the number of total image pixels.

We calculated the compression factor as $$CF = \left(1 - \frac{k}{250}\frac{1}{2}m\right) * 100 \quad (1)$$

where the factor of ½ accounts for the missing imaginary part.

Training and Hyperparameter Optimization

At each iteration, the networks predict a new estimate $\hat{y}_i$, and the parameters are learned using the Adam optimizer [32] with $\beta_1=0.9$, $\beta_2=0.999$, and $\varepsilon=10^{-7}$ to minimize the loss function $$L(y, \hat{y}) = \lambda L_{SSIM}(y, \hat{y}) + (1 - \lambda) L_{MAE}(y, \hat{y}) \quad (2)$$

with $$L_{MAE}(y, \hat{y}) = \frac{1}{n}\sum_{i=1}^{n} \frac{\|y_i - \hat{y}_i\|_1}{N} \quad (3)$$

$$L_{SSIM}(y, \hat{y}) = \frac{1}{n}\sum_{i=1}^{n} 1 - SSIM(y_i, \hat{y}_i). \quad (4)$$

In the above equations, y denotes the SoA training images, $\|\cdot\|_1$ the $l_1$ norm, N the number of image pixels, and n the number of examples. The structural dissimilarity index metric loss $L_{SSIM}$ is a perceptual loss based on the structural similarity index metric (SSIM), which integrates luminance, contrast, and structural information [33]. A kernel of 3×3 pixels was used for the SSIM calculation. We considered the learning rate and the parameter $\lambda$ as hyperparameters, and their optimal value was determined via Bayesian optimization.

We based our quantitative performance analysis on the SSIM of the reconstructed images versus the respective SoA images, the normalized mean squared error NMSE=$\|y_i-\hat{y}_i\|_2/\|y_i\|_2$, with $\|\cdot\|_2$ the $l_2$ norm, and on the peak signal-to-noise ratio (PSNR). We implemented the networks in Python using TensorFlow 2.1 with Keras API. The networks were trained on a single NVIDIA Titan RTX GPU with 24 GB of RAM. The mini-batch size was set to 1 in all the experiments.

For each network, we first optimized the hyperparameters using the Bayesian optimization routine in the Keras Tuner library. We ran 15 optimization trials using the sparse dataset with CF 75%. The optimization routine was instructed to maximize the validation SSIM. Each trial trained the reconstruction CNNs for 2500 epochs and selected the model with the best performance. The results of the optimal hyperparameter search for all the networks are reported in Table I. Then, we trained the CNNs with the optimal hyperparameters using CFs of 80%, 85%, 90%, and 95%. We trained the Deep-fUS network for 1500 epochs (we noted that the CNN converged faster during optimization), the U-Net for 2500 epochs, and the PP-U-Net for 500 epochs. In all trainings, the model with the best validation SSIM was saved.

Ultrasound System and Data Acquisition

For ultrasound data acquisition, we used two 128-element linear array transducers (L22-14vX and L22-14vLF; Verasonics Inc.) operating at a 15-MHz center frequency with a Vantage 256 research scanner (Verasonics Inc.). The probes are geometrically identical apart from the focus in the elevation plane; the L22-14vX is focused at a distance of 8 mm, and the L22-14vLF is focused at 20 mm. For exact positioning relative to the skull landmarks, the imaging probe was housed in a custom 3-D printed holder mounted on a motorized positioning system. Ultrasound gel was used for acoustic coupling. We used tilted plane waves at angle (−6°, −3°, 0°, 3°, 6°) emitted with a pulse repetition frequency of 19 kHz. Two plane waves were averaged for each angle to increase the signal-to-noise ratio, giving a total of 10 emissions per compound frame. We acquired data for 250 compound frames at a rate of 1 kHz (i.e., a new sequence of compound frames every 250 ms), and the data for each compound sequence (250·10 emissions) were transferred in batch to the host computer. Compound frames were created by beamforming the received sensor RF data in a regular grid of pixels of 100 µm×100 µm in an NVIDIA Titan RTX GPU using a GPU beamformer [34]. Ultrasound data were acquired asynchronously and continuously, i.e., a new sequence of frames was acquired during processing of the previous sequence and held in the scanner buffer until the host computer was available. The compound frames were saved on the host machine for offline processing. The final power Doppler frame rate was 0.6 frames/s.

Conventional Power Doppler Processing

Sequences of compound ultrasound frames were processed in Matlab (MathWorks) for clutter filtration and power Doppler computation. We used a 5th-order temporal high-pass Butterworth filter with a cutoff frequency of 40 Hz cascaded with an SVD filter that eliminates the first singular value [8]. In the Doppler space, frequencies are linearly proportional to the velocity of the scatterers from which the Doppler signal originated. Therefore, it is expected that signals emanating from the slowly moving tissue surrounding the blood vessels (clutter) are positioned at around 0 Hz, and this assumption justifies the use a temporal high-pass filter. Singular value decomposition filters are instead based on the assumption that, while blood signals are highly incoherent due to the time-varying stochastic distribution of the moving scatterers (red blood cells), tissue signals maintain a high degree of correlation over time, and therefore aim to eliminate the highly coherent components. At each pixel location (x, y), the intensity of the filtered signal was then calculated to find the power Doppler value I(x, y)=~$s^2$(x, y, t)dt (shown as 106 in FIG. 1A). For the SoA processing (250 complex compound frames), the entire time window of 250 ms was integrated.

Animal Preparation and Imaging Experiments

Long Evans and Sprague Dawley rats (Charles River; n=15; age 10-14 weeks; weight 260-400 g) were used in this study. We prepared the animals by performing a bilateral surgical craniotomy and chronic prosthesis implant using previously published protocols [7]. Briefly, animals were anesthetized with 3.5% isoflurane in $O_2$ and anesthesia was maintained with 1.5% isoflurane. Rats were placed in a stereotaxic frame during surgery for head fixation and orientation. Body temperature was monitored by a rectal probe and maintained at 36.5° C. using a warming pad (RightTemp Jr.; Kent Scientific). A pulse oximeter was used to monitor heart rate and arterial oxygen saturation (MouseStat Jr.; Kent Scientific). We administered anti-inflammatory to prevent brain swelling and inflammation (1 mg/kg dexamethasone intraperitoneally). After a skin incision was performed, parietal and frontal skull bone fragments (AP +4 to −9 mm; ML ±6 mm) were cut using a handheld high-speed drill with a 0.7 mm drill bit (Fine Science Tools). We gently removed the bone flaps, paying special attention to avoid any damage to the dura mater. We used dental cement (Tetric EvoFlow; Ivoclar Vivadent) to seal a 125 µm thick polymethylpentene prosthesis covering the entire craniotomy. The bone was pre-treated with a bonding agent (iBOND Total Etch; Kulzer). The space between the dura mater and the polymer prosthesis was filled with 0.9% sterile saline. Animals were then allowed to recover for 1 week before the first imaging session.

During the imaging sessions, animals were either anesthetized and kept under anesthesia with 1.5% isoflurane while placed in a stereotaxic frame or were lightly sedated with 0.5% isoflurane and kept in a restraining apparatus [35]. The restrained imaging protocol was also used in the lightly sedated fUS experiment of FIG. 6. Coronal slices of the rat brain recorded between 2.7 mm anterior and 7.04 mm posterior to bregma [36].

Visual Stimulation Protocol and Functional Activity Maps

To evaluate whether the present Deep-fUS technique provides sufficient accuracy in the reconstruction of time series of power Doppler images in a functional neuroimaging application, we imaged visual task-evoked brain activation in rats exposed to binocular green light stimulation. Rats were anesthetized, placed in a stereotaxic frame, and kept in a dark chamber for at least 30 min prior to the visual stimulation session for dark adaptation. Bilateral visual stimuli were delivered using two green light LEDs driven by a custom power supply circuit. We controlled the stimulus pattern through a microcontroller board (Arduino Uno) connected to Matlab via the serial port and interfaced with the Verasonics scanner for synchronization with the imaging sequence. For each light stimulus, the LEDs were flashed for 30 s at a frequency of 3 Hz. Each stimulus was followed by a >30 s pause in a pseudo-random fashion. This stimulation protocol was shown to maximize visual cortex response in prior fUS imaging studies [37].

Functional activation maps were created by calculating the Pearson's correlation coefficient r between the temporal power Doppler signal and the stimulus pattern [1], [8]. We used a Fisher's transformation to calculate the z score as $$z = \frac{1}{2}\sqrt{N-3}\ln\frac{1+r}{1-r} \quad (5)$$

with N the number of temporal samples. Each pixel was considered significant for z>3.1 (corresponding to P<0.001 in a one-tailed t-test). We used this threshold to create binary activation maps that only show the significant pixels.

Results

Figure 2B:
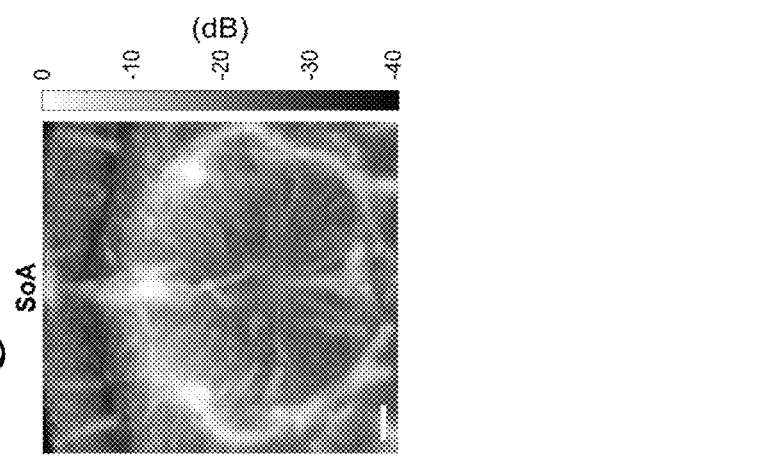
FIG. 2B is an image reconstructed by the conventional processing using complex compound frames.

The received sensor RF data from 10 plane wave emissions were beamformed in a regular grid of 96×96 pixels with a spatial resolution of 100 µm×100 µm to create compound frames. Sequences of compound frames were then processed to compute the power Doppler images. The conventional processing achieves a satisfactory level of detail in coronal brain images reconstructed from 250 complex compound frames as shown in the SoA image of FIG. 2B.

The resulting SoA images were used for the CNN training and as a reference for evaluating the reconstruction performance. To test the power Doppler reconstruction with sub-optimal conditions, we retrospectively created sparse data sequences by selecting subsamples of k compound frames from each sequence, with a compression factor (CF) of 75% (k=125), 80% (k=100), 85% (k=75), 90% (k=50) and 95% (k=25). Power Doppler images reconstructed by the conventional processing from under-sampled data appear increasingly noisy due to the reduced blood flow sensitivity. This is illustrated in FIG. 2C, which shows power Doppler images reconstructed with the conventional processing using under-sampled compound data (Top) and respective absolute error images (Bottom) with CF of 75%, 85%, and 95%.

Deep-fUS Power Doppler Reconstruction

The Deep-fUS network blindly solves a reconstruction problem to directly extract the power Doppler values from a sequence of compound frames. The network takes in input a sparse compound sequence and outputs the corresponding power Doppler image. The results of the Bayesian hyper-parameter optimization are reported in Table I.

TABLE I

Results of Bayesian optimization

| Network | Hyperparameter | Optimized value |
|---|---|---|
| Deep-fUS | Conv3D, $k_{1,2}$ | 3 |
|  | Conv3D, $k_3$ | 16 |
|  | Learning rate | $5.5 \times 10^{-4}$ |
|  | Dropout rate | 0.2 |
|  | Lambda | 0.1 |
| 3D-U-Net | Conv3D, $k_{1,2}$ | 1 |
|  | Conv3D, $k_3$ | 16 |
|  | Learning rate | $1.1 \times 10^{-4}$ |
|  | Dropout rate | 0.1 |
|  | Lambda | 0.9 |
| U-Net | Learning rate | $7.4 \times 10^{-5}$ |
|  | Dropout rate | 0.2 |
|  | Lambda | 0.8 |
| PP-U-Net | Learning rate | $7.4 \times 10^{-4}$ |
|  | Dropout rate | 0.1 |
|  | Lambda | 0.2 |

Figure 2A:
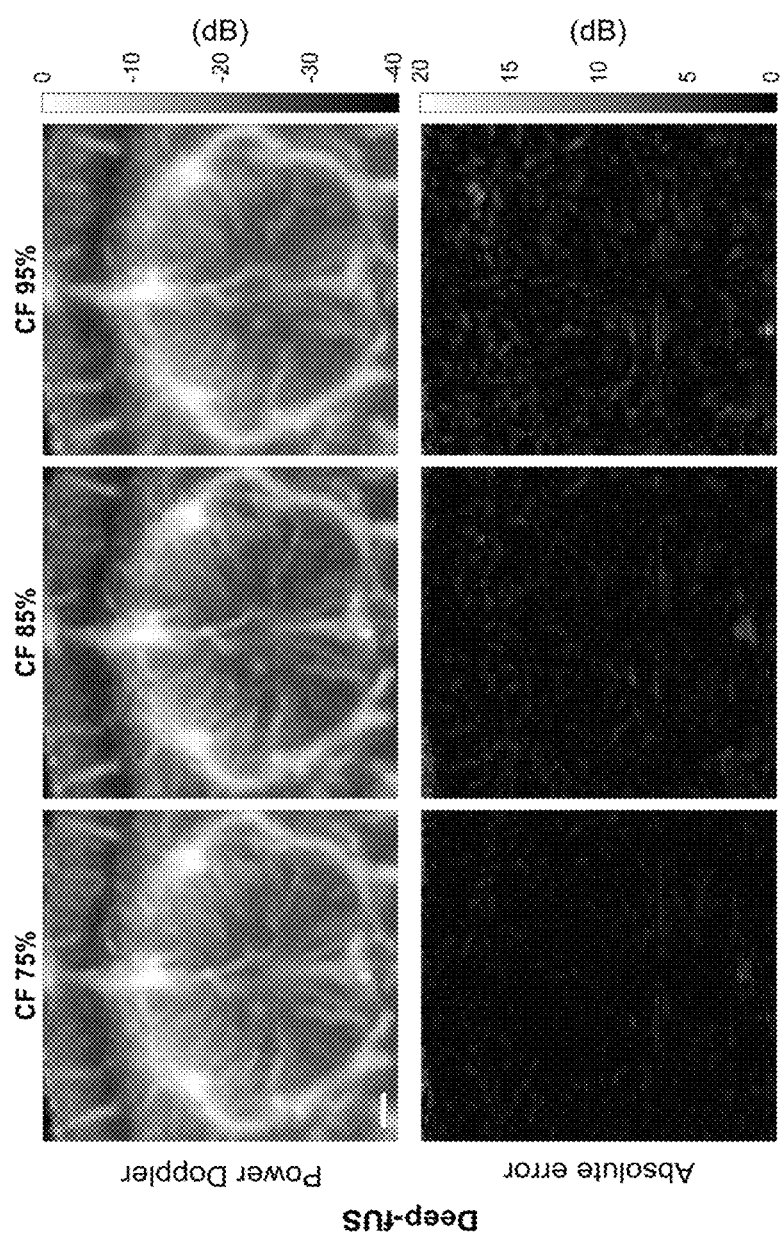
FIG. 2A is a collection of images showing a representative power Doppler image reconstructed by Deep-fUS from under-sampled sequences with compression factor (CF) 75%, 85%, and 95% (top row) and absolute error images calculated against the state-of-the-art (SoA) image (bottom row).

The Deep-fUS network restores the reference imaging performance and is able to reconstruct the rat brain micro-vasculature from sparse data with a CF up to 95%. This is illustrated in FIG. 2A, which shows representative power Doppler image of a coronal slice of the rat brain reconstructed by Deep-fUS from under-sampled sequences with compression factor (CF) 75%, 85%, and 95% (Top) and absolute error images calculated against the state-of-the-art (SoA) image (Bottom).

Figure 3A:
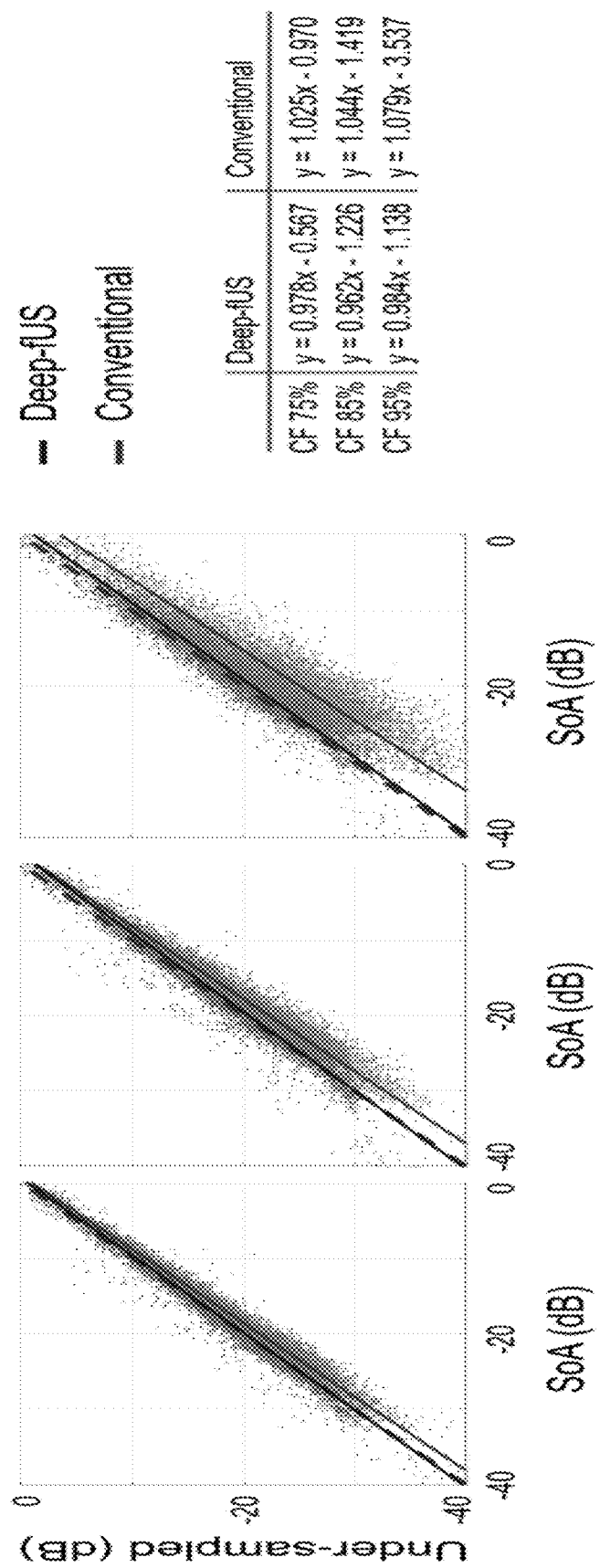
FIG. 3A shows scatter plots of the power Doppler pixel amplitudes and linear regression analysis, which highlight that reconstruction errors are more prominent in correspondence of the lower power Doppler values, particularly in the case of conventional processing.
Figure 3B:
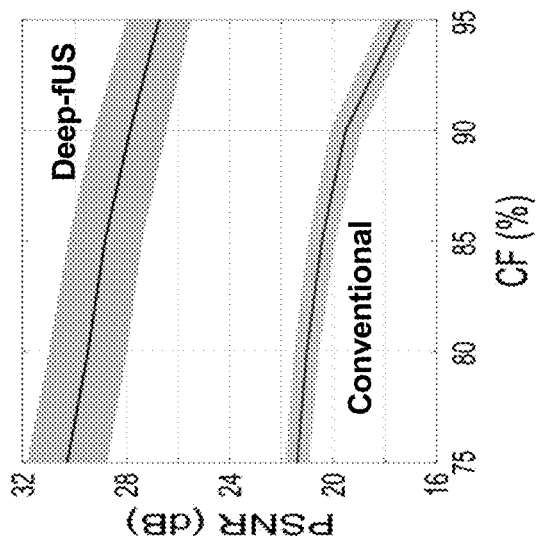
FIGS. 3B, 3C, 3D are plots of structural similarity index metric (SSIM), normalized mean squared error (NMSE), and peak signal-to-noise ratio (PSNR), respectively, of power Doppler images reconstructed by Deep-fUS and by the conventional approach.
Figure 3C:
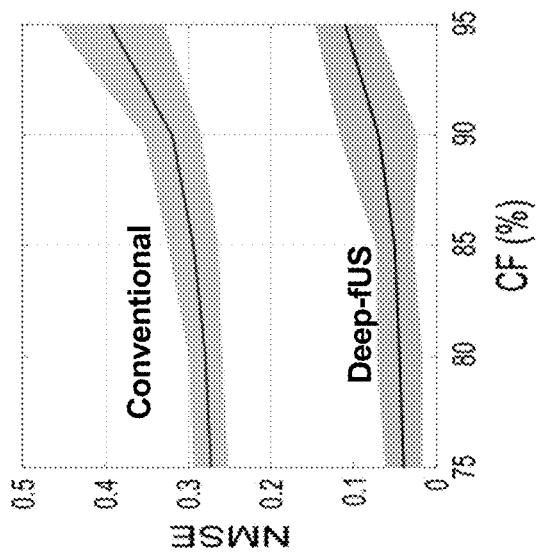
Figure 3D:
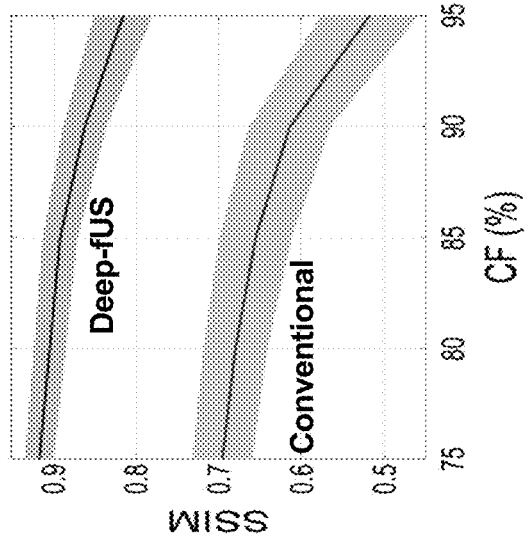

The CNN produces a considerable improvement in the under-sampled power Doppler reconstruction when compared to the conventional processing, as confirmed by the quantitative metrics in FIG. 3B-3D. These figures show the structural similarity index metric (SSIM), normalized mean squared error (NMSE), and peak signal-to-noise ratio (PSNR), respectively, of power Doppler images reconstructed by Deep-fUS and by the conventional approach. The quantitative metrics were calculated against the respective SoA reference images. Results are reported as mean (solid line) and standard deviation (shaded area) calculated over the test set.

FIG. 3A shows scatter plots of the power Doppler pixel amplitudes and linear regression analysis ($y=b_1+b_2$). The scatter plots highlight that reconstruction errors are more prominent in correspondence of the lower power Doppler values, is particularly in the case of conventional processing. While all the trained CNNs perform significantly better than the conventional processing when sparse data are used, the Deep-fUS network achieves superior reconstruction performance, with maximum SSIM of 0.92, PSNR of 30 dB, and NMSE of 0.04. We note that the introduction of the 3-D convolutional input layer is responsible for 91% of the SSIM improvement and 77% of the NMSE reduction. While all the trained CNNs performed significantly better than the conventional processing when sparse data are used, the DeepfUS network achieved overall superior reconstruction performance, with maximum SSIM of 0.92, PSNR of 30.29 dB, and minimum NMSE of 0.04. Introducing the 3-D convolutional input layer resulted in a maximum SSIM improvement of 0.07 (CF 75%), PSNR improvement of 2.16 dB (CF 80%), and NMSE reduction of 0.08 (CF 95%).

TABLE II

Quantitative performance metrics

| NETWORK | CF | SSIM | PSNR (dB) | NMSE | ACTIVATION MAP MAE |
|---|---|---|---|---|---|
| Deep-fUS (reconstruction) | 75% | 0.9166 ± 0.0174 | 30.2851 ± 1.5516 | 0.0399 ± 0.0222 | 0.0952 |
| | 80% | 0.9041 ± 0.0192 | 29.4798 ± 1.5038 | 0.0448 ± 0.0278 | 0.1077 |
| | 85% | 0.8915 ± 0.0211 | 28.8217 ± 1.4282 | 0.0506 ± 0.0224 | 0.1171 |
| | 90% | 0.8619 ± 0.0264 | 27.8481 ± 1.4058 | 0.0701 ± 0.0472 | 0.1315 |
| | 95% | 0.8154 ± 0.0353 | 26.7270 ± 1.2469 | 0.1106 ± 0.0364 | 0.1805 |
| 3D-U-Net (reconstruction) | 75% | 0.9046 ± 0.0189 | 29.5322 ± 1.4163 | 0.0647 ± 0.0259 | 0.1132 |
| | 80% | 0.8981 ± 0.0201 | 29.4254 ± 1.2746 | 0.0652 ± 0.0335 | 0.1253 |
| | 85% | 0.8874 ± 0.0202 | 29.0893 ± 1.2615 | 0.0728 ± 0.0308 | 0.1265 |
| | 90% | 0.86 ± 0.0238 | 28.2881 ± 1.2772 | 0.0913 ± 0.0464 | 0.1579 |
| | 95% | 0.8139 ± 0.0373 | 27.1319 ± 0.7524 | 0.1177 ± 0.0495 | 0.1837 |
| U-Net (reconstruction) | 75% | 0.8394 ± 0.0342 | 27.6412 ± 0.7867 | 0.1222 ± 0.0488 | 0.1202 |
| | 80% | 0.8348 ± 0.0323 | 27.2672 ± 0.7142 | 0.1375 ± 0.0456 | 0.1315 |
| | 85% | 0.8384 ± 0.0325 | 27.3371 ± 0.8499 | 0.1399 ± 0.0385 | 0.1326 |
| | 90% | 0.8237 ± 0.0337 | 26.7846 ± 0.8862 | 0.1398 ± 0.0467 | 0.1369 |
| | 95% | 0.7927 ± 0.0444 | 26.1352 ± 0.8169 | 0.1946 ± 0.0550 | 0.1592 |
| PP-U-Net (post-processing) | 75% | 0.9269 ± 0.0153 | 31.1037 ± 1.2606 | 0.0359 ± 0.0239 | 0.1017 |
| | 80% | 0.9165 ± 0.0179 | 30.6757 ± 1.4619 | 0.0396 ± 0.0224 | 0.1109 |
| | 85% | 0.902 ± 0.0212 | 30.2345 ± 1.1474 | 0.0459 ± 0.0242 | 0.1356 |
| | 90% | 0.876 ± 0.0233 | 29.1286 ± 1.3275 | 0.061 ± 0.0323 | 0.1538 |
| | 95% | 0.8226 ± 0.0376 | 27.3628 ± 0.9142 | 0.102 ± 0.0537 | 0.1626 |
| Conventional | 75% | 0.6955 ± 0.0362 | 21.3873 ± 0.4584 | 0.2726 ± 0.0208 | 0.2030 |
| | 80% | 0.6799 ± 0.0387 | 21.0242 ± 0.4763 | 0.2793 ± 0.0202 | 0.2275 |
| | 85% | 0.6553 ± 0.0438 | 20.4423 ± 0.5235 | 0.2938 ± 0.0303 | 0.2467 |
| | 90% | 0.6142 ± 0.0497 | 19.5135 ± 0.6068 | 0.3193 ± 0.0349 | 0.2760 |
| | 95% | 0.5181 ± 0.0585 | 17.4375 ± 0.6265 | 0.3947 ± 0.0652 | 0.2952 |

The residual connections were responsible for a further maximum SSIM increase of 0.01, PSNR increase of 0.75 dB, and NMSE reduction of 0.02, all in the CF 75% case. The Deep-fUS network with both the 3-D convolutional input layer and residual connections also provided overall better performance in the computation of functional activation maps, for which we report the mean absolute error (MAE) in Table II.

The mean prediction time for the Deep-fUS network is between 4.4 and 13.5 ms/image. The post-processing U-Net provides comparable imaging performance but adds a time overhead of ~210 ms/image for the pre-processing of the sparse power Doppler images (Table III). It is also worth noting that this approach is like the conventional method, in that it is inherently dependent on the design of the tissue clutter filter. Interestingly, we noted that the learned convolutional filters in the input layer of the Deep-fUS network implement high-pass transfer functions with strong rejection of the 0-Hz component (see FIGS. 1D-1E). These filters appear to mimic the temporal filters used in the conventional processing but are learned directly from the data during training.

TABLE III

Network parameters and processing times

| Network | | Deep-fUS | 3D-U-Net | U-Net | PP-U-Net |
|---|---|---|---|---|---|
| N. Layers | | 5 + 1 | 5 + 1 | 5 | 5 |
| N. trainable parameters | | 9,788,421 | 8,773,701 | 8,665,633 | 8,629,921 |
| Training epochs | | 1500 | 1500 | 2500 | 500 |
| Processing time (ms/img) | CF 75% | 13.5 | 7.12 | 5.28 | 2.06 + 255.7 |
| | CF 80% | 11.1 | 5.67 | 4.6 | 2.04 + 220.3 |
| | CF 85% | 9.2 | 4.77 | 3.88 | 2.09 + 207.2 |
| | CF 90% | 6.7 | 3.89 | 3.34 | 2.08 + 194.8 |
| | CF 95% | 4.4 | 2.95 | 2.66 | 2.04 + 183.4 |

Task-Evoked Functional Activity Imaging

FIG. 4A illustrates the processing of a time series sequence of power Doppler images 400 recorded continuously during a visual stimulation task. The resulting cerebral blood volume (CBV) signals 402 were Pearson correlated 406 with the stimulus pattern 404 to produce a correlation coefficient 408. The stimulation had 6 light stimuli, each with an ON time of 30 s, distributed in a pseudo-random fashion.

The SoA activation map is shown for reference in FIG. 4B. This was computed using power Doppler images reconstructed by the conventional approach using 250 complex compound frames. The activation map (heat map) is superimposed on a power Doppler image. The white contour represents the slice at bregma −7.04 mm from the Paxinos brain atlas. The activation map shows significant bilateral activation of the rat primary and secondary visual cortices (V1M/V1B/V2MM).

Figure 4C:
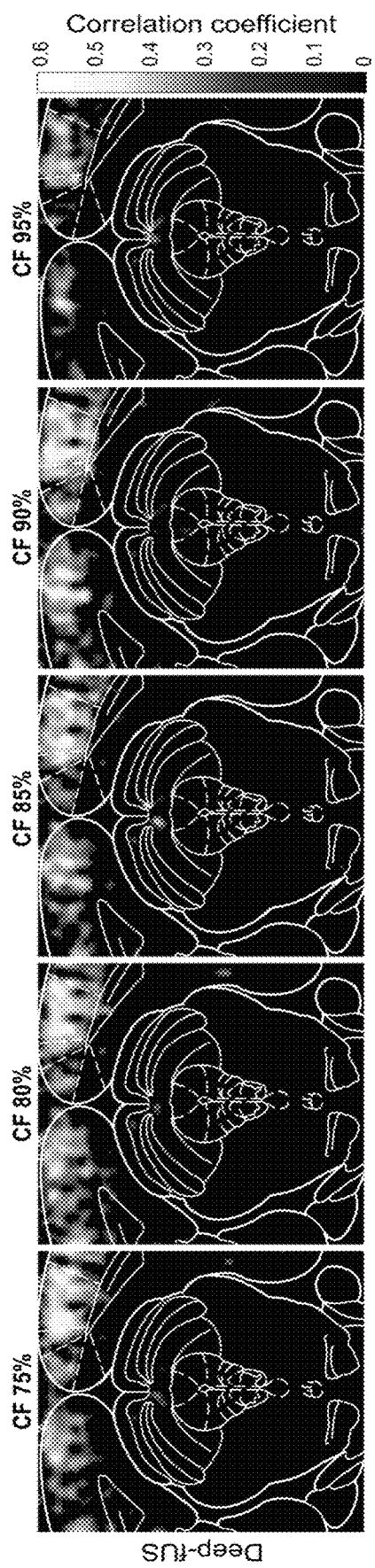
FIG. 4C show images of activation maps computed using power Doppler images reconstructed by Deep-fUS with compression factor (CF) between 75% and 95%.
Figure 4D:
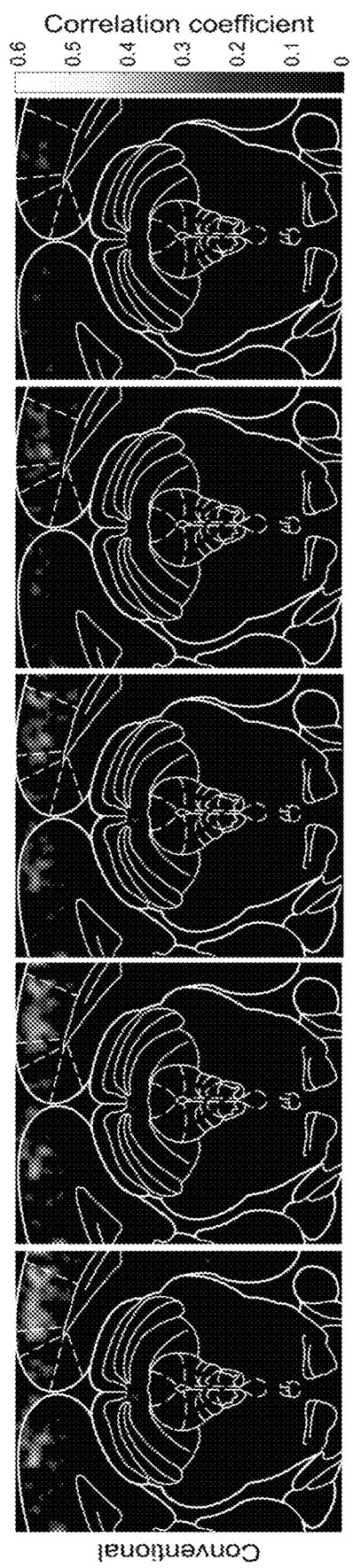
FIG. 4D show images of activation maps computed using power Doppler images reconstructed by conventional processing with CF between 75% and 95%.
Figure 4E:
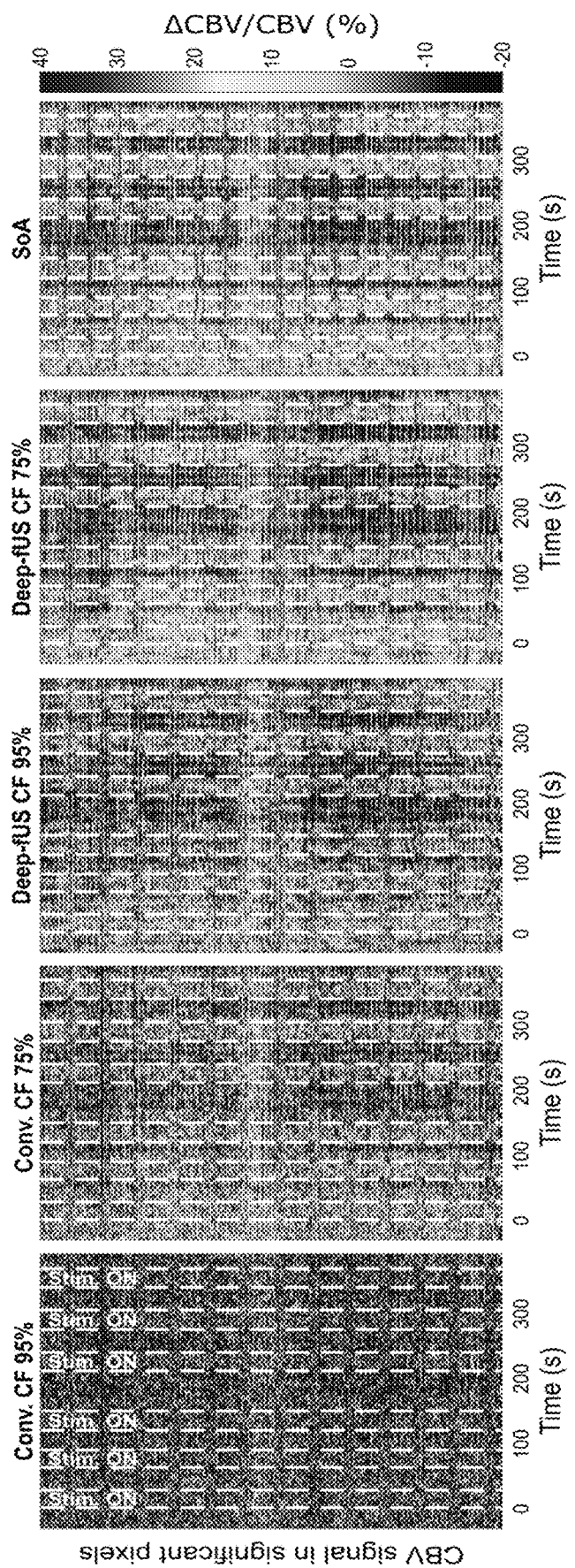
FIG. 4E are plots illustrating relative CBV signals in all the statistically significant pixels of the SoA map in FIG. 4B.

In FIG. 4C we show the activation maps computed using power Doppler time series reconstructed by Deep-fUS using sparse data with CF between 75% and 95%. Although the quality of the activation maps degrades with increasing data sparsity, significant visual cortex activation can be detected with a CF up to 95%. FIG. 4D shows activation maps computed using power Doppler images reconstructed by conventional processing with CF between 75% and 95%. Notably, Deep-fUS with CF 95% performs better than the conventional approach with CF 75%. With shorter data sequences (i.e., higher CF), the conventional processing provides increasingly noisy CBV temporal signals that result in lower and non-significant correlations with the stimulus. This is illustrated in FIG. 4E, which shows plots of relative CBV signals in all the statistically significant pixels of the SoA map in FIG. 4B. The dashed vertical lines show the stimulus ON/OFF times. These results are also confirmed by the quantitative error metric (MAE) in Table II. Introducing the 3-D convolutional input layer and residual connections reduced the activation maps MAE in all the cases except for CF 95%, as compared to the simple U-Net. This may be due to the short temporal signals that make it more challenging to train the 3-D filters.

Our network generalized well to the reconstruction of time series of power Doppler images and was able to detect the small changes in relative CBV signal (~10%; see FIG. 4E) characteristic of visual-evoked cortical activation, although it was not formally trained to perform this reconstruction task.

We then created temporally and spatially under-sampled sequences by retaining only a subset of compound samples in each frame, with a spatial under-sampling ratio m=½ and m=¼. We selected k=50 and k=100 in the two cases to equalize the CF to 95%. This approach improved the quality of the functional activation maps compared to the case with temporal under-sampling only, and suggests that spatial sparsity may be a viable option to further increase data compression while retaining the advantages of longer acquisitions. This is illustrated in FIG. 5A-5B which show representative power Doppler test images and activation maps computed with spatially under-sampled sequences with spatial sampling ratio m=½ (FIG. 5A) and m=¼ (FIG. 5B). To equalize the compression factor (CF) to 95%, k=50 and k=100 compound frames were used in the two cases.

Motion Artifact Reduction

Figure 6A:
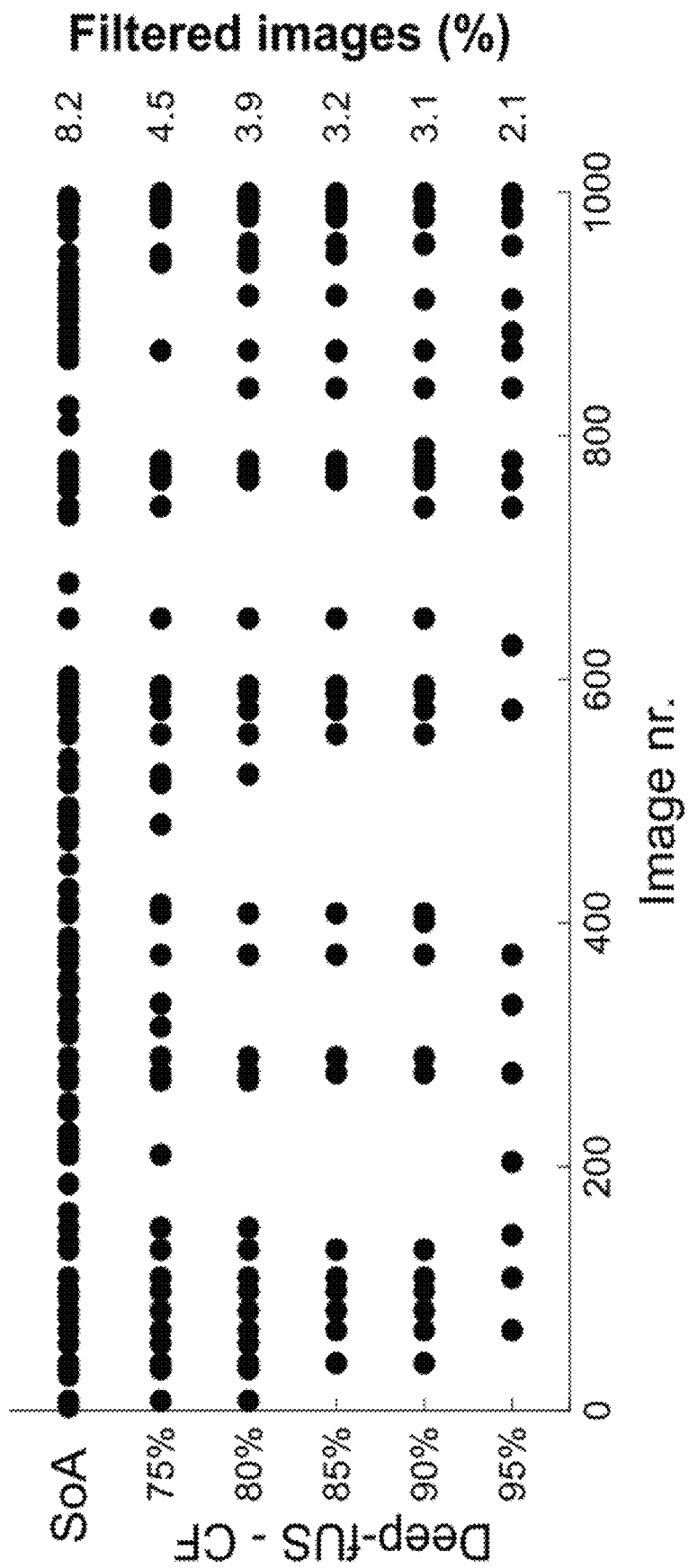
FIG. 6A is a plot showing the results of a series of power Doppler images filtered based on a structural similarity index metric (SSIM) filter.

To determine whether shorter acquisition sequences reduce the occurrence of motion artifacts, we used Deep-fUS to reconstruct a time series of power Doppler images acquired in a lightly sedated and restrained animal. We computed the SSIM of each image in the series versus a baseline calculated as the median of all images in the acquisition, then we applied a SSIM threshold to filter out the images that showed significant degradation, possibly due to animal motion. In the case of SoA processing using the full compound sequence, 8.2% of power Doppler images were discarded by the filter. FIG. 6A illustrates results of a series of 1000 power Doppler images filtered based on a structural similarity index metric (SSIM) filter. Black dots display the discarded images in the series.

Figure 6B:
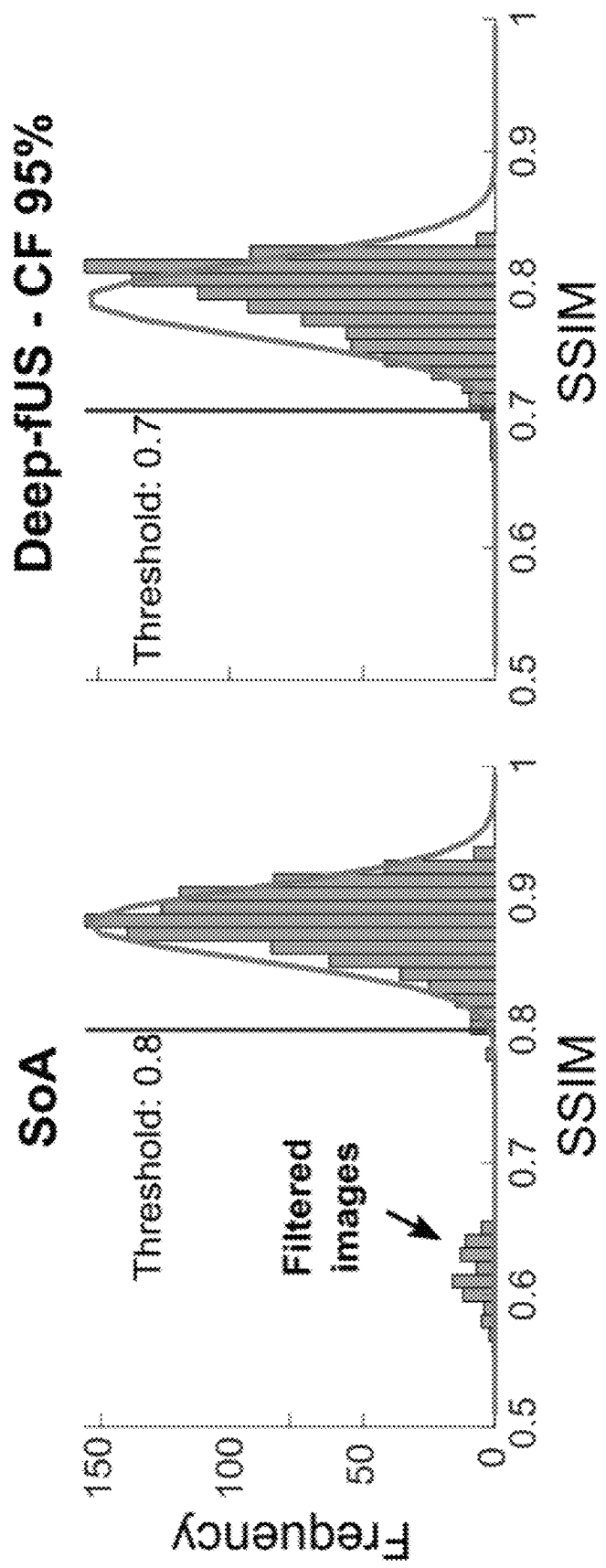
FIG. 6B are plots illustrating thresholds used to remove the images with an SSIM value lower than 3 standard deviations from the baseline.
Figure 6D:
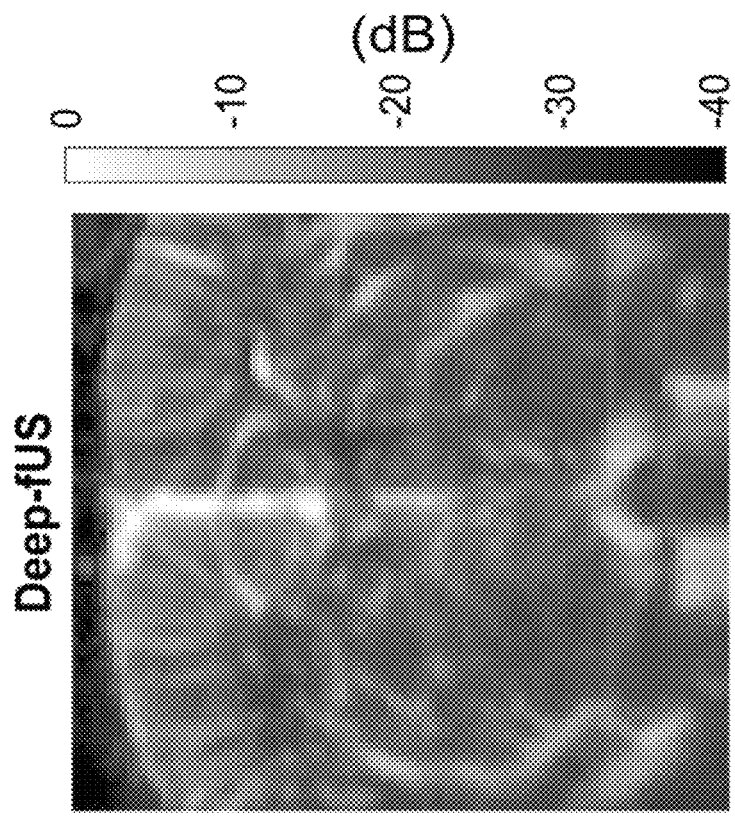
FIG. 6C-D show representative power Doppler coronal images in a case of significant degradation in the conventional reconstruction (FIG. 6C) and using under-sampled processing (FIG. 6D).
Figure 6C:

Image scrubbing was reduced to between 4.5% (with CF 75%) and 2.1% (with CF 95%), giving a maximum scrubbing reduction of 74%. FIG. 6B illustrates how a threshold was used to remove the images with an SSIM value lower than 3 standard deviations from the baseline. FIG. 6C displays a representative SoA power Doppler image that was discarded by the SSIM filter. Motion artifacts were resolved in same image processed by Deep-fUS as shown in FIG. 6D. These representative power Doppler coronal images contrast the significant degradation in the conventional reconstruction (FIG. 6C) with under-sampled Deep-fUS processing (FIG. 6D) which completely resolved the degradation.

Discussion

Deep learning and CNNs are drawing increasing attention for the reconstruction and processing of biomedical images with sparse data [38]-[40]. In medical ultrasound, several strategies have been proposed to restore high image quality while reducing data sampling, transmission, and processing [27], [28], [30], [41]. With the exception of a single preliminary study reporting deep learning of color Doppler images [42], however, CNNs have not been applied as extensively to ultrasound imaging of blood flows. We have disclosed here a deep learning method for the direct reconstruction of power Doppler images from a 3-D space of sparse compound ultrasound data (FIG. 1A). This approach largely enhanced imaging performance compared to the conventional method with compression factors up to 95%, as clearly indicated by the presented quantitative metrics (FIGS. 3A-D). We demonstrated that the network is able to reconstruct time series of power Doppler is images with sufficient accuracy to compute functional activation maps in a task-evoked neuroimaging application (FIG. 4A-E and FIG. 5A-B). Although it was not formally trained on such a reconstruction task, the network generalized well and detected changes in relative CBV signals on the order of 10%. Additionally, we show that by minimizing the length of the acquisition sequence, our network allows greater robustness to motion artifacts in an experiment with a lightly sedated animal and is less sensitive to image scrubbing (FIG. 6A-D).

The main advantage of using sparse sequences is the net reduction in data acquisition, storage, and processing demands. The approach of the present invention can facilitate the development of fUS neuroimaging in any setting where dedicated hardware is not available or in clinical scanners, making this technology more affordable and opening the way to new potential applications based on this imaging modality. Additionally, sparse sequences may prove beneficial in experimental situations where fUS acquisitions need to be interleaved with long therapeutic ultrasound pulses, such as in the monitoring of focused ultrasound neurointerventions [43], [44]. Importantly, this method significantly reduces the exposure time and lowers the risk of harmful bioeffects, making brain ultrasound neuroimaging safer [3], [18].

Although in this study we retrospectively under-sampled the compound data, we clearly demonstrate that the network may considerably reduce the beamforming complexity and eliminate the need for computationally demanding filters [14], [15]. Additionally, the network has the potential to increase the imaging frame rate and to facilitate the implementation of volumetric fUS imaging using swept linear arrays [6]. The platform and conceptual framework that we propose may be adapted to other high-frame-rate Doppler ultrasound imaging modalities, including vector flow imaging, to expedite their deployment in portable ultrasound systems [45], [46]. In creating sparse sequences, we chose to select only the initial portion of the original sequence instead of selecting and retaining interleaved frames to take advantage of the shorter temporal acquisition windows. This approach has the benefit of reducing the occurrence of motion artifacts and signal degradation due to data scrubbing, which are inevitable factors in mobile rodent fUS imaging experiments [8], [47] and handheld applications [5] and are more likely to appear with longer acquisition times.

Although variants of the U-Net have been previously applied to different biomedical imaging modalities, most of the literature is focused on removing artifacts from suboptimally reconstructed images. We were specifically interested in demonstrating a data-driven reconstruction method that, once trained, requires no prior model-based knowledge of the image formation process nor requires hand-picked parameters. We decided to base our implementation on the U-Net as we hypothesized that its encoder-decoder architecture would fit the nature of our data.

A critical step in the power Doppler reconstruction process is the filtration of the strong clutter signal originating from the moving tissue. In the 3-D space formed by the image plane and Doppler time, the clutter signal is slowly varying in the temporal domain and highly correlated in the spatial domain, therefore it is crucial to account for both spatially and temporally varying features in the reconstruction process. By progressively expanding the spatial field of view in the encoder layers and with the input filters performing temporal convolutions, our network extracts spatiotemporal features from severely under-sampled input datasets. By using more sophisticated networks, interesting applications may be developed in the future based on the current work. Unsupervised algorithms may be designed to train variants of generative adversarial networks (for example, CycleGAN [48]) on 2-D power Doppler images for the reconstruction of volumetric fUS data acquired with sparse physical apertures. Considering the cost, complexity, and bulkiness of 3-D ultrasound systems, such advances may greatly facilitate 4-D fUS imaging applications.

A main limitation of using ultrasound for brain imaging is the presence of the skull, which is highly absorbing at the imaging frequencies. This has limited clinical fUS to intraoperative applications or to scenarios with natural skull openings, such as the neonatal anterior fontanel window. The reduced data required by the present method could facilitate implementations of fUS with focused emissions, which may prove more efficient in the presence of the skull.

REFERENCES

[1] E. Macé, G. Montaldo, I. Cohen, M. Baulac, M. Fink, and M. Tanter, "Functional ultrasound imaging of the brain," *Nat. Methods*, vol. 8, no. 8, pp. 662-664, 2011.

[2] E. Macè et al., "Whole-Brain Functional Ultrasound Imaging Reveals Brain Modules for Visuomotor Integration," *Neuron*, vol. 100, no. 5, pp. 1241-1251.e7, 2018.

[3] C. Demené et al., "Functional ultrasound imaging of brain activity in human newborns," *Sci. Transl. Med.*, vol. 9, no. 411, 2017.

[4] M. Imbault, D. Chauvet, J. L. Gennisson, L. Capelle, and M. Tanter, "Intraoperative Functional Ultrasound Imaging of Human Brain Activity," *Sci Rep.*, vol. 7, no. 1, pp. 1-7, 2017.

[5] S. Soloukey et al., "Functional Ultrasound (fUS) During Awake Brain Surgery: The Clinical Potential of Intra-Operative Functional and Vascular Brain Mapping," *Front. Neurosci*, vol. 13, no. January, pp. 1-14, 2020.

[6] J. Baranger et al., "Bedside functional monitoring of the dynamic brain connectivity in human neonates," *Nat. Commun.*, vol. 12, no. 1, 2021.

[7] L.-A. Sieu et al., "EEG and functional ultrasound imaging in mobile rats," *Nat. Methods*, vol. 12, no. 9, pp. 831-834, 2015.

[8] A. Urban, C. Dussaux, G. Martel, C. Brunner, E. Mace, and G. Montaldo, "Real-time imaging of brain activity in freely moving rats using functional ultrasound," *Nat. Methods*, vol. 12, no. 9, pp. 873-878, 2015.

[9] B. F. Osmanski, S. Pezet, A. Ricobaraza, Z. Lenkei, and M. Tanter, "Functional ultrasound imaging of intrinsic connectivity in the living rat brain with high spatiotemporal resolution," *Nat. Commun.*, vol. 5, 2014.

[10] J. Ferrier, E. Tiran, T. Deffieux, M. Tanter, and Z. Lenkei, "Functional imaging evidence for task-induced deactivation and disconnection of a major default mode network hub in the mouse brain," *Proc. Natl. Acad. Sci. U.S.A.*, vol. 117, no. 26, pp. 15270-15280, 2020.

[11] K. Blaize et al., "Functional ultrasound imaging of deep visual cortex in awake nonhuman primates," *Proc. Natl. Acad. Sci. U.S.A.*, vol. 117, no. 25, pp. 14453-14463, 2020.

[12] A. Dizeux et al., "Functional ultrasound imaging of the brain reveals propagation of task-related brain activity in behaving primates," *Nat. Commun.*, vol. 10, no. 1, pp. 1-9, 2019.

[13] S. L. Norman et al., "Single-trial decoding of movement intentions using functional ultrasound neuroimaging," *Neuron*, pp. 1-13, March 2021.

[14] C. Demené et al., "Spatiotemporal Clutter Filtering of Ultrafast Ultrasound Data Highly Increases Doppler and fUltrasound Sensitivity," *IEEE Trans. Med. Imaging*, vol. 34, no. 11, pp. 2271-2285, 2015.

[15] J. Baranger, B. Arnal, F. Perren, O. Baud, M. Tanter, and C. Demene, "Adaptive Spatiotemporal SVD Clutter Filtering for Ultrafast Doppler Imaging Using Similarity of Spatial Singular Vectors," *IEEE Trans. Med. Imaging*, vol. 37, no. 7, pp. 1574-1586, 2018.

[16] C. Rabut et al., "4D functional ultrasound imaging of whole-brain activity in rodents," *Nat. Methods*, vol. 16, no. 10, pp. 994-997, 2019.

[17] J. Sauvage et al., "4D Functional Imaging of the Rat Brain Using a Large Aperture Row-Column Array," *IEEE Trans. Med. Imaging*, vol. 39, no. 6, pp. 1884-1893, 2020.

[18] E. S. B. C. Ang, V. Gluncic, A. Duque, M. E. Schafer, and P. Rakic, "Prenatal exposure to ultrasound waves impacts neuronal migration in mice," *Proc. Natl. Acad. Sci. U.S.A.*, vol. 103, no. 34, pp. 12903-12910, 2006.

[19] O. Ronneberger, P. Fischer, and T. Brox, "U-net: Convolutional networks for biomedical image segmentation," *Lect. Notes Comput. Sci. (including Subser. Lect. Notes Artif Intell. Lect. Notes Bioinformatics)*, vol. 9351, pp. 234-241, 2015.

[20] G. Yang et al., "DAGAN: Deep De-Aliasing Generative Adversarial Networks for Fast Compressed Sensing MRI Reconstruction," *IEEE Trans. Med. Imaging*, vol. 37, no. 6, pp. 1310-1321, 2018.

[21] N. Davoudi, X. L. Dean-Ben, and D. Razansky, "Deep learning optoacoustic tomography with sparse data," *Nat. Mach. Intell.*, vol. 1, no. 10, pp. 453-460, October 2019.

[22] K. H. Jin, M. T. Mccann, E. Froustey, and M. Unser, "Deep Convolutional Neural Network for Inverse Problems in Imaging," *IEEE Trans. Image Process.*, vol. 26, no. 9, pp. 4509-4522, 2017.

[23] A. C. Luchies and B. C. Byram, "Deep Neural Networks for Ultrasound Beamforming," *IEEE Trans. Med. Imaging*, vol. 37, no. 9, pp. 2010-2021, 2018.

[24] D. Hyun, L. L. Brickson, K. T. Looby, and J. J. Dahl, "Beamforming and speckle reduction using neural networks," *IEEE Trans. Ultrason. Ferroelectr. Freq. Control*, vol. 66, no. 5, pp. 898-910, 2019.

[25] D. Hyun, L. Abou-Elkacem, R. Bam, L. L. Brickson, C. D. Herickhoff, and J. J. Dahl, "Nondestructive Detection of Targeted Microbubbles Using Dual-Mode Data and Deep Learning for Real-Time Ultrasound Molecular Imaging," *IEEE Trans. Med. Imaging*, vol. 39, no. 10, pp. 3079-3088, 2020.

[26] J. Youn, M. L. Ommen, M. B. Stuart, E. V. Thomsen, N. B. Larsen, and J. A. Jensen, "Detection and Localization of Ultrasound Scatterers Using Convolutional Neural Networks," *IEEE Trans. Med. Imag.*, 2020.

[27] M. Gasse, F. Millioz, E. Roux, D. Garcia, H. Liebgott, and D. Friboulet, "High-quality plane wave compounding using convolutional neural networks," *IEEE Trans. Ultrason. Ferroelectr. Freq. Control*, vol. 64, no. 10, pp. 1637-1639, 2017.

[28] Y. H. Yoon, S. Khan, J. Huh, and J. C. Ye, "Efficient B-Mode Ultrasound Image Reconstruction From Sub-Sampled RF Data Using Deep Learning," *IEEE Trans. Med. Imaging*, vol. 38, no. 2, pp. 325-336, 2019.

[29] B. Luijten et al., "Adaptive Ultrasound Beamforming using Deep Learning," *IEEE Trans. Med. Imag.*, pp. 1-12, 2019.

[30] A. A. Nair, K. N. Washington, T. D. Tran, A. Reiter, and M. A. Lediju Bell, "Deep Learning to Obtain Simultaneous Image and Segmentation Outputs From a Single Input of Raw Ultrasound Channel Data," *IEEE Trans. Ultrason. Ferroelectr. Freq. Control*, vol. 67, no. 12, pp. 2493-2509, December 2020.

[31] K. He, X. Zhang, S. Ren, and J. Sun, "Deep residual learning for image recognition," *Proc. IEEE Comput. Soc. Conf. Comput. Vis. Pattern Recognit.*, pp. 770-778, 2016.

[32] D. P. Kingma and J. L. Ba, "Adam: A method for stochastic optimization," *3rd Int. Conf. Learn. Represent. ICLR 2015—Conf. Track Proc.*, pp. 1-15, 2015.

[33] Z. Wang, A. C. Bovik, H. R. Sheikh, and E. P. Simoncelli, "Image quality assessment: From error visibility to structural similarity," *IEEE Trans. Image Process.*, vol. 13, no. 4, pp. 600-612, 2004.

[34] D. Hyun, G. E. Trahey, and J. J. Dahl, "Real-time high-framerate in vivo cardiac SLSC imaging with a GPU-based beamformer," *2015 IEEE Int. Ultrason. Symp. IUS 2015*, pp. 1-4, 2015.

[35] P. Stenroos et al., "Awake rat brain functional magnetic resonance imaging using standard radio frequency coils and a 3D printed restraint kit," *Front. Neurosci.*, vol. 12, no. August, 2018.

[36] G. Paxinos and C. Watson, *The Rat Brain in Stereotaxic Coordinates: Hard Cover Edition*. Academic Press, 1998.

[37] M. Gesnik et al., "3D functional ultrasound imaging of the cerebral visual system in rodents," *Neuroimage*, vol. 149, no. October 2016, pp. 267-274, 2017.

[38] B. Zhu, J. Z. Liu, S. F. Cauley, B. R. Rosen, and M. S. Rosen, "Image reconstruction by domain-transform manifold learning," *Nature*, vol. 555, no. 7697, pp. 487-492, 2018.

[39] V. Vishnevskiy, J. Walheim, and S. Kozerke, "Deep variational network for rapid 4D flow MRI reconstruction," *Nat. Mach. Intell.*, vol. 2, no. 4, pp. 228-235, April 2020.

[40] L. Shen, W. Zhao, and L. Xing, "Patient-specific reconstruction of volumetric computed tomography images from a single projection view via deep learning," *Nat. Biomed. Eng.*, vol. 3, no. 11, pp. 880-888, 2019.

[41] A. Wiacek, E. Gonzalez, and M. A. L. Bell, "CohereNet: A Deep Learning Architecture for Ultrasound Spatial Correlation Estimation and Coherence-Based Beamforming," *IEEE Trans. Ultrason. Ferroelectr. Freq. Control*, vol. 67, no. 12, pp. 2574-2583, December 2020.

[42] I. A. M. Huijben, B. S. Veeling, K. Janse, M. Mischi, and R. J. G. Van Sloun, "Learning Sub-Sampling and Signal Recovery with Applications in Ultrasound Imaging," *IEEE Trans. Med. Imaging*, vol. 39, no. 12, pp. 3955-3966, 2020.

[43] J. B. Wang et al., "Focused Ultrasound for Noninvasive, Focal Pharmacologic Neurointervention," *Front. Neurosci.*, vol. 14, no. July, 2020.

[44] J. B. Wang, M. Aryal, Q. Zhong, D. B. Vyas, and R. D. Airan, "Noninvasive Ultrasonic Drug Uncaging Maps Whole-Brain Functional Networks," *Neuron*, vol. 100, pp. 728-738, 2018.

[45] T. Di Ianni et al., "A Vector Flow Imaging Method for Portable Ultrasound Using Synthetic Aperture Sequential Beamforming," *IEEE Trans. Ultrason. Ferroelectr. Freq. Control*, vol. 64, no. 11, pp. 1655-1665, November 2017.

[46] T. Di Ianni, C. A. V. Hoyos, C. Ewertsen, M. B. Nielsen, and J. A. Jensen, "High-frame-rate imaging of a carotid bifurcation using a low-complexity velocity estimation approach," in *IEEE International Ultrasonics Symposium, IUS*, 2017.

[47] C. Rabut et al., "Pharmaco-fUS: Quantification of pharmacologically-induced dynamic changes in brain perfusion and connectivity by functional ultrasound imaging in awake mice," *Neuroimage*, vol. 222, no. August, p. 117231, 2020.

[48] Z. Ma, F. Wang, W. Wang, Y. Zhong, and H. Dai, "Deep learning for in vivo near-infrared imaging," *Proc. Natl. Acad. Sci. U.S.A.*, vol. 118, no. 1, pp. 1-8, 2021.

The invention claimed is:

1. A method for ultrasound power Doppler image reconstruction comprising:
 obtaining sparse temporal sequences of compound frames of ultrasound data, wherein the sparse temporal sequences are undersampled by at least 75% compared with fully-sampled data;
 inputting the sparse temporal sequences into a convolutional neural network;
 generating as output from the convolutional neural network a reconstructed time series of power Doppler images corresponding to the sparse temporal sequences;
 wherein the convolutional neural network is trained to learn a power Doppler reconstruction function that maps a sequence of compound frames to a corresponding power Doppler image, wherein the convolutional neural network generates the power Doppler image as output at a final layer of the convolutional neural network from the sequence of compound frames input at a first layer of the convolutional neural network, wherein the convolutional neural network is trained using ground truth images from high-quality in vivo images, wherein the convolutional neural network is trained using a custom loss function.

2. The method of claim 1 wherein the convolutional neural network is a U-Net with drop-out layers.

3. The method of claim 1 wherein the convolutional neural network is a U-Net with an input layer of 3D convolutional filters that extract spatiotemporal features from the sparse temporal sequences.

4. The method of claim 1 wherein the custom loss function is defined as a weighted sum of 1) a mean absolute error between a predicted Deep-fUS image and a respective ground truth (LMAE) and 2) a structural dissimilarity index metric loss (LSSIM).

5. The method of claim 1 wherein the ultrasound power Doppler image reconstruction is performed in real-time intrasurgically for guidance and monitoring.

6. The method of claim 1 wherein the ultrasound power Doppler image reconstruction is performed in real-time in procedures in newborn through the fontanel window by reducing data acquisition, storage, and processing resources, and by reducing sensitivity to motion artifacts.

* * * * *